(12) United States Patent
Bazan et al.

(10) Patent No.: US 8,546,081 B2
(45) Date of Patent: Oct. 1, 2013

(54) METHODS AND COMPOSITIONS FOR ASSAYING A SAMPLE FOR AN AGGREGANT

(75) Inventors: Guillermo C. Bazan, Santa Barbara, CA (US); Bin Liu, Singapore (SG)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/367,358

(22) Filed: Feb. 6, 2012

(65) Prior Publication Data

US 2012/0214255 A1 Aug. 23, 2012

Related U.S. Application Data

(60) Division of application No. 12/711,233, filed on Feb. 23, 2010, now Pat. No. 8,110,673, which is a continuation of application No. 11/344,942, filed on Jan. 31, 2006, now Pat. No. 7,666,594.

(60) Provisional application No. 60/649,024, filed on Jan. 31, 2005.

(51) Int. Cl.
*C12Q 1/68* (2006.01)
*G01N 33/53* (2006.01)

(52) U.S. Cl.
USPC ............................................ 435/6.1; 435/7.1

(58) Field of Classification Search
USPC ...................................................... 435/6.1, 7.1
See application file for complete search history.

(56) References Cited

U.S. PATENT DOCUMENTS

| 7,214,489 | B2 * | 5/2007 | Bazan et al. | 435/6.11 |
|---|---|---|---|---|
| 7,270,956 | B2 * | 9/2007 | Bazan et al. | 435/6.19 |
| 2005/0003386 | A1 * | 1/2005 | Bazan et al. | 435/6 |
| 2006/0183140 | A1 * | 8/2006 | Bazan et al. | 435/6 |
| 2006/0216734 | A1 * | 9/2006 | Bazan et al. | 435/6 |

* cited by examiner

*Primary Examiner* — Kenneth Horlick
(74) *Attorney, Agent, or Firm* — Bozicevic, Field & Francis LLP; Bret E. Field

(57) ABSTRACT

This invention relates to an aggregation sensor useful for the detection and analysis of aggregants in a sample, and methods, articles and compositions relating to such a sensor. The sensor comprises first and second optically active units, where energy may be transferred from an excited state of the first optically active unit to the second optically active unit. The second optically active unit is present in a lesser amount, but its relative concentration is increased upon aggregation, increasing its absorption of energy from the first optically active units. This increase in energy transfer can be detected in variety of formats to produce an aggregation sensing system for various aggregants, including for quantitation. Other variations of the inventions are described further herein.

18 Claims, 9 Drawing Sheets

METHODS AND COMPOSITIONS FOR ASSAYING A SAMPLE FOR AN AGGREGANT

CROSS REFERENCE TO RELATED APPLICATIONS

This application is a divisional of U.S. patent application Ser. No. 12/711,233, filed Feb. 23, 2010, now U.S. Pat. No. 8,110,673 issued Feb. 6, 2012, which in turn is a continuation of U.S. patent application Ser. No. 11/344,942, filed Jan. 31, 2006, now U.S. Pat. No. 7,666,594 issued Feb. 23, 2010, which claims the benefit of U.S. Provisional Application No. 60/649,024, filed Jan. 31, 2005. The aforementioned applications are hereby incorporated herein by reference in their entirety, including the drawings.

STATEMENT REGARDING FEDERALLY SPONSORED RESEARCH

This invention was made with Government support under Grant No. DMR-0097611 awarded by the National Science Foundation and Grant No. N00014-98-0759 awarded by the Office of Naval Research. The U.S. Government has certain rights in this invention.

SEQUENCE LISTING

The instant application contains a Sequence Listing which has been submitted in ASCII format via EFS-Web and is hereby incorporated by reference in its entirety. Said ASCII copy, created on Apr. 27, 2012, is named 20042874 SequenceListing.txt and is 1,516 kilobytes in size.

TECHNICAL FIELD

This invention relates to an aggregation sensor useful for the detection and analysis of aggregants in a sample, and methods, articles and compositions relating to such a sensor.

BACKGROUND OF THE INVENTION

Methods for the detection of biomolecules such as nucleic acids are highly significant not only in identifying specific targets, but also in understanding their basic function. Hybridization probe technologies in particular continue to be one of the most essential elements in the study of gene-related biomolecules.[1,2,3] They are useful for a variety of both commercial and scientific applications, including the identification of genetic mutations or single nucleotide polymorphisms (SNP's), medical diagnostics, gene delivery, assessment of gene expression, and drug discovery.[4,5,6,7]

Conjugated polymers have proven useful as light gathering molecules in a variety of settings. Conjugated polymers soluble in polar media have proven particularly useful. Water-soluble conjugated polymers such as cationic conjugated polymers (CCPs) have been used in bioassays to improve detection sensitivity and provide new routes of selectivity in analyzing biomolecules.

There is a continuing need in the art for methods of detecting and analyzing particular biomolecules in a sample, and for compositions and articles of manufacture useful in such methods. There is a need in the art for novel CCPs, for methods of making and using them, and for compositions and articles of manufacture comprising such compounds.

DETAILED DESCRIPTION OF THE INVENTION

Figure 1A:
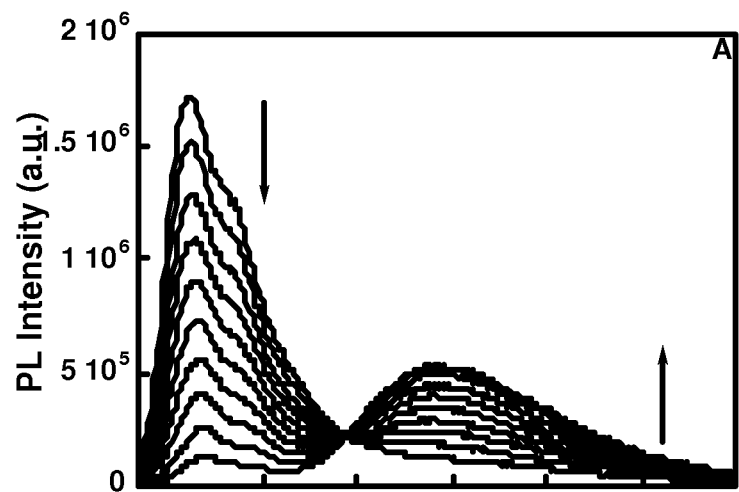
FIG. 1(A). Fluorescence spectra of PFPB in water as a function of [ss-DNA] ([RU]=5×10$^{-7}$ M, [ss-DNA]=0 M to 2.7×10$^{-8}$ M in 3.0×10$^{-9}$ M increments, $\lambda_{exc}$=380 nm). (B) Normalized photoluminescence spectra of PFP (a) the absorption (b) and emission (c) spectra of ss-DNA-TR in water.

DNA and RNA detection methods are of considerable scientific and technological importance.[8,9,10] Water-soluble conjugated polymers are of particular interest for this purpose because their molecular structure allows for collective response and, therefore, optical amplification of fluorescent signals.[11,12] The large number of optically active units along the polymer chain increases the probability of light absorption, relative to small molecule counterparts.[12] Facile fluorescence resonance energy transfer (FRET) makes it possible to deliver excitations to fluorophores, which signal the presence of a target DNA sequence.[13,14]

Recent studies indicate that energy transfer between segments in conjugated polymers may be substantially more important than along the backbone.[15,16] External perturbations that decrease the elongation of the backbone, or that bring segments closer together, can therefore be used to substantially modify the emissive properties of a polymer in solution.

Based on these observations, it occurred to us that a small number of fluorescent units within a polymer sequence could be activated by structural changes that compressed or aggregated the polymer chains to ultimately change the emission color. We designed a cationic conjugated polymer structure that incorporates these design guidelines. Electrostatic complexation with negatively charged DNA can be used to reduce the average intersegment distance. When combined with a fluorophore labeled peptide nucleic acid (PNA) strand, the polymer can be used to design a three color DNA detection assay.

These working examples are demonstrations of a broader principle: that of an aggregation sensor that provides a signal that varies depending on its state of aggregation. The aggregation sensor comprises first optically active units that dominate its spectrum in the absence of aggregant, and a lesser proportion of second optically active units capable of receiving energy from an excited state of the first optically active units. In the presence of an aggregant, the sensor becomes aggregated, and energy is transferred to the second optically active units. The emission from the first optically active units decreases. The second optically active units may disperse the energy non-radiatively, may emit light of a characteristic wavelength, or may be used to transfer energy to a subsequent fluorophore, series of fluorophores, or quencher.

The aggregation sensor binds to a class of aggregants through a component having an affinity for the aggregant. The affinity component may be an ionic region that can interact with an oppositely charged region on the aggregant, or the aggregant and aggregation sensor may comprise members of a binding pair. The examples utilize a polycationic region in the sensor, and a negatively charged polynucleotide as an aggregant. Presence of the polynucleotide in a sample leads to aggregation of the sensor, causing a change in its emission and energy transfer to second optically active units present in a smaller amount. Those second optically active units may transfer energy to a subsequent optically active molecule, which is exemplified as a fluorophore, but can be a quencher.

The inventions described herein are useful for any assay in which a sample can be interrogated regarding an aggregant. Typical assays involve determining the presence of the aggregant in the sample or its relative amount, or the assays may be quantitative or semi-quantitative.

The methods can be performed on a substrate. The assay can be performed in an array format on a substrate, which can be a sensor. These substrates may be surfaces of glass, silicon, paper, plastic, or the surfaces of optoelectronic semiconductors (such as, but not confined to, indium-doped gallium nitride or polyanilines, etc.) employed as optoelectronic transducers.

The methods of the invention can be performed in multiplex formats. In some embodiments, a plurality of different probes can be used to detect corresponding different species of aggregants in a sample through the use of different signaling chromophores conjugated to the respective probes or through the use of localization of particular probes to determinable regions of the substrate. Multiplex methods are provided employing 2, 3, 4, 5, 10, 15, 20, 25, 50, 100, 200, 400 or more different probes which can be used simultaneously to assay for corresponding different aggregants of interest. It is further envisioned that in certain embodiments, for example in high density arrays, the number of different probes used simultaneously could be 500, $1 \times 10^3$, $1 \times 10^4$, $1 \times 10^5$, $1 \times 10^6$ or more different probes.

Before the present invention is described in further detail, it is to be understood that this invention is not limited to the particular methodology, devices, solutions or apparatuses described, as such methods, devices, solutions or apparatuses can, of course, vary. It is also to be understood that the terminology used herein is for the purpose of describing particular embodiments only, and is not intended to limit the scope of the present invention.

Use of the singular forms "a," "an," and "the" include plural references unless the context clearly dictates otherwise. Thus, for example, reference to "an aggregation sensor" includes a plurality of aggregation sensors, reference to "a probe" includes a plurality of probes, and the like. Additionally, use of specific plural references, such as "two," "three," etc., read on larger numbers of the same subject less the context clearly dictates otherwise.

Terms such as "connected," "attached," "conjugated" and "linked" are used interchangeably herein and encompass direct as well as indirect connection, attachment, linkage or conjugation unless the context clearly dictates otherwise; in one example, the phrase "conjugated polymer" is used in accordance with its ordinary meaning in the art and refers to a polymer containing an extended series of unsaturated bonds, and that context dictates that the term "conjugated" should be interpreted as something more than simply a direct or indirect connection, attachment or linkage.

Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention, as are ranges based thereon. Where a combination is disclosed, each subcombination of the elements of that combination is also specifically disclosed and is within the scope of the invention. Conversely, where different elements or groups of elements are disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Unless defined otherwise or the context clearly dictates otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

All publications mentioned herein are hereby incorporated by reference for the purpose of disclosing and describing the particular materials and methodologies for which the reference was cited. The publications discussed herein are provided solely for their disclosure prior to the filing date of the present application. Nothing herein is to be construed as an admission that the invention is not entitled to antedate such disclosure by virtue of prior invention.

DEFINITIONS

In describing the present invention, the following terms will be employed, and are intended to be defined as indicated below.

The term "aggregation" and the like refer to a relative increase in the concentration of the second optically active subunit(s) of an aggregation sensor within a particular volume, which may be a localized region of a larger volume. The term encompasses any form of accumulation, compaction, condensing, etc., that increases the ability to transfer energy from an excited first optically active unit(s) to a second optically active unit, including without limitation alteration(s) of the conformation of a single aggregation sensor, the bringing together of different aggregation sensors, or both.

"Alkyl" refers to a branched, unbranched or cyclic saturated hydrocarbon group of 1 to 24 carbon atoms optionally substituted at one or more positions, and includes polycyclic compounds. Examples of alkyl groups include optionally substituted methyl, ethyl, n-propyl, isopropyl, n-butyl, s-butyl, t-butyl, n-pentyl, isopentyl, neopentyl, n-hexyl, n-heptyl, n-octyl, n-decyl, hexyloctyl, tetradecyl, hexadecyl, eicosyl, tetracosyl and the like, as well as cycloalkyl groups such as cyclopropyl, cyclobutyl, cyclopentyl, cyclohexyl, cycloheptyl, cyclooctyl, adamantyl, and norbornyl. The term "lower alkyl" refers to an alkyl group of 1 to 6 carbon atoms, preferably 1 to 4 carbon atoms. Exemplary substituents on substituted alkyl groups include hydroxyl, cyano, alkoxy, =O, =S, —NO$_2$, halogen, haloalkyl, heteroalkyl, carboxyalkyl, amine, amide, thioether and —SH.

"Alkoxy" refers to an "-Oalkyl" group, where alkyl is as defined above. A "lower alkoxy" group intends an alkoxy group containing one to six, more preferably one to four, carbon atoms.

"Alkenyl" refers to a branched, unbranched or cyclic hydrocarbon group of 2 to 24 carbon atoms containing at least one carbon-carbon double bond optionally substituted at one or more positions. Examples of alkenyl groups include ethenyl, 1-propenyl, 2-propenyl (allyl), 1-methylvinyl, cyclopropenyl, 1-butenyl, 2-butenyl, isobutenyl, 1,4-butadienyl, cyclobutenyl, 1-methylbut-2-enyl, 2-methylbut-2-en-4-yl, prenyl, pent-1-enyl, pent-3-enyl, 1,1-dimethylallyl, cyclopentenyl, hex-2-enyl, 1-methyl-1-ethylallyl, cyclohexenyl, heptenyl, cycloheptenyl, octenyl, cyclooctenyl, decenyl, tetradecenyl, hexadecenyl, eicosenyl, tetracosenyl and the like. Preferred alkenyl groups herein contain 2 to 12 carbon atoms. The term "lower alkenyl" intends an alkenyl group of 2 to 6 carbon atoms, preferably 2 to 4 carbon atoms. The term "cycloalkenyl" intends a cyclic alkenyl group of 3 to 8, preferably 5 or 6, carbon atoms. Exemplary substituents on substituted alkenyl groups include hydroxyl, cyano, alkoxy, =O, =S, —NO$_2$, halogen, haloalkyl, heteroalkyl, amine, thioether and —SH.

"Alkenyloxy" refers to an "-Oalkenyl" group, wherein alkenyl is as defined above.

"Alkylaryl" refers to an alkyl group that is covalently joined to an aryl group. Preferably, the alkyl is a lower alkyl. Exemplary alkylaryl groups include benzyl, phenethyl, phenopropyl, 1-benzylethyl, phenobutyl, 2-benzylpropyl and the like.

"Alkylaryloxy" refers to an "-Oalkylaryl" group, where alkylaryl is as defined above.

"Alkynyl" refers to a branched or unbranched hydrocarbon group of 2 to 24 carbon atoms containing at least one —C≡C— triple bond, optionally substituted at one or more positions. Examples of alkynyl groups include ethynyl, n-propynyl, isopropynyl, propargyl, but-2-ynyl, 3-methylbut-1-ynyl, octynyl, decynyl and the like. Preferred alkynyl groups herein contain 2 to 12 carbon atoms. The term "lower alkynyl" intends an alkynyl group of 2 to 6, preferably 2 to 4, carbon atoms, and one —C≡C— triple bond. Exemplary substituents on substituted alkynyl groups include hydroxyl, cyano, alkoxy, =O, =S, —NO$_2$, halogen, haloalkyl, heteroalkyl, amine, thioether and —SH.

"Amide" refers to —C(O)NR'R", where R' and R" are independently selected from hydrogen, alkyl, aryl, and alkylaryl.

"Amine" refers to an —N(R')R" group, where R' and R" are independently selected from hydrogen, alkyl, aryl, and alkylaryl.

"Aryl" refers to an aromatic group that has at least one ring having a conjugated pi electron system and includes carbocyclic, heterocyclic, bridged and/or polycyclic aryl groups, and can be optionally substituted at one or more positions. Typical aryl groups contain 1 to 5 aromatic rings, which may be fused and/or linked. Exemplary aryl groups include phenyl, furanyl, azolyl, thiofuranyl, pyridyl, pyrimidyl, pyrazinyl, triazinyl, biphenyl, indenyl, benzofuranyl, indolyl, naphthyl, quinolinyl, isoquinolinyl, quinazolinyl, pyridopyridinyl, pyrrolopyridinyl, purinyl, tetralinyl and the like. Exemplary substituents on optionally substituted aryl groups include alkyl, alkoxy, alkylcarboxy, alkenyl, alkenyloxy, alkenylcarboxy, aryl, aryloxy, alkylaryl, alkylaryloxy, fused saturated or unsaturated optionally substituted rings, halogen, haloalkyl, heteroalkyl, —S(O)R, sulfonyl, —SO$_3$R, —SR, —NO$_2$, —NRR', —OH, —CN, —C(O)R, —OC(O)R, —NHC(O)R, —(CH$_2$)$_n$CO$_2$R or —(CH$_2$)$_n$CONRR' where n is 0-4, and wherein R and R' are independently H, alkyl, aryl or alkylaryl.

"Aryloxy" refers to an "-Oaryl" group, where aryl is as defined above.

"Carbocyclic" refers to an optionally substituted compound containing at least one ring and wherein all ring atoms are carbon, and can be saturated or unsaturated.

"Carbocyclic aryl" refers to an optionally substituted aryl group wherein the ring atoms are carbon.

"Halo" or "halogen" refers to fluoro, chloro, bromo or iodo. "Halide" refers to the anionic form of the halogens.

"Haloalkyl" refers to an alkyl group substituted at one or more positions with a halogen, and includes alkyl groups substituted with only one type of halogen atom as well as alkyl groups substituted with a mixture of different types of halogen atoms. Exemplary haloalkyl groups include trihalomethyl groups, for example trifluoromethyl.

"Heteroalkyl" refers to an alkyl group wherein one or more carbon atoms and associated hydrogen atom(s) are replaced by an optionally substituted heteroatom, and includes alkyl groups substituted with only one type of heteroatom as well as alkyl groups substituted with a mixture of different types of heteroatoms. Heteroatoms include oxygen, sulfur, and nitrogen. As used herein, nitrogen heteroatoms and sulfur heteroatoms include any oxidized form of nitrogen and sulfur, and any form of nitrogen having four covalent bonds including protonated forms. An optionally substituted heteroatom refers to replacement of one or more hydrogens attached to a nitrogen atom with alkyl, aryl, alkylaryl or hydroxyl.

"Heterocyclic" refers to a compound containing at least one saturated or unsaturated ring having at least one heteroatom and optionally substituted at one or more positions. Typical heterocyclic groups contain 1 to 5 rings, which may be fused and/or linked, where the rings each contain five or six atoms. Examples of heterocyclic groups include piperidinyl, morpholinyl and pyrrolidinyl. Exemplary substituents for optionally substituted heterocyclic groups are as for alkyl and aryl at ring carbons and as for heteroalkyl at heteroatoms.

"Heterocyclic aryl" refers to an aryl group having at least 1 heteroatom in at least one aromatic ring. Exemplary heterocyclic aryl groups include furanyl, thienyl, pyridyl, pyridazinyl, pyrrolyl, N-lower alkyl-pyrrolo, pyrimidyl, pyrazinyl, triazinyl, tetrazinyl, triazolyl, tetrazolyl, imidazolyl, bipyridyl, tripyridyl, tetrapyridyl, phenazinyl, phenanthrolinyl, purinyl and the like.

"Hydrocarbyl" refers to hydrocarbyl substituents containing 1 to about 20 carbon atoms, including branched, unbranched and cyclic species as well as saturated and unsaturated species, for example alkyl groups, alkylidenyl groups, alkenyl groups, alkylaryl groups, aryl groups, and the like. The term "lower hydrocarbyl" intends a hydrocarbyl group of one to six carbon atoms, preferably one to four carbon atoms.

A "substituent" refers to a group that replaces one or more hydrogens attached to a carbon or nitrogen. Exemplary substituents include alkyl, alkylidenyl, alkylcarboxy, alkoxy, alkenyl, alkenylcarboxy, alkenyloxy, aryl, aryloxy, alkylaryl, alkylaryloxy, —OH, amide, carboxamide, carboxy, sulfonyl, =O, =S, —NO$_2$, halogen, haloalkyl, fused saturated or unsaturated optionally substituted rings, —S(O)R, —SO$_3$R, —SR, —NRR', —OH, —CN, —C(O)R, —OC(O)R, —NHC(O)R, —(CH2)$_n$CO$_2$R or —(CH2)$_n$CONRR' where n is 0-4, and wherein R and R' are independently H, alkyl, aryl or alkylaryl. Substituents also include replacement of a carbon atom and one or more associated hydrogen atoms with an optionally substituted heteroatom.

"Sulfonyl" refers to —S(O)$_2$R, where R is alkyl, aryl, —C(CN)=C-aryl, —CH$_2$CN, alkylaryl, or amine.

"Thioamide" refers to —C(S)NR'R", where R' and R" are independently selected from hydrogen, alkyl, aryl, and alkylaryl.

"Thioether" refers to —SR, where R is alkyl, aryl, or alkylaryl.

As used herein, the term "binding pair" refers to first and second molecules that bind specifically to each other with greater affinity than to other components in the sample. The binding between the members of the binding pair is typically noncovalent. Exemplary binding pairs include immunological binding pairs (e.g. any haptenic or antigenic compound in combination with a corresponding antibody or binding portion or fragment thereof, for example digoxigenin and anti-digoxigenin, fluorescein and anti-fluorescein, dinitrophenol and anti-dinitrophenol, bromodeoxyuridine and anti-bromodeoxyuridine, mouse immunoglobulin and goat anti-mouse immunoglobulin) and nonimmunological binding pairs (e.g., biotin-avidin, biotin-streptavidin, hormone [e.g., thyroxine and cortisol]-hormone binding protein, receptor-receptor agonist or antagonist (e.g., acetylcholine receptor-acetylcholine or an analog thereof) IgG-protein A, lectin-carbohydrate, enzyme-enzyme cofactor, enzyme-enzyme-inhibitor, and complementary polynucleotide pairs capable of forming nucleic acid duplexes) and the like. One or both member of the binding pair can be conjugated to additional molecules.

The terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. These terms refer only to the primary structure of the molecule. Thus, the terms includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide.

Whether modified or unmodified, in some embodiments a target nucleotide has a polyanionic backbone, preferably a sugar-phosphate background, of sufficient negative charge to electrostatically interact with a polycationic multichromophore in the methods described herein, although other forces may additionally participate in the interaction. A sensor polynucleotide can be used that is a peptide nucleic acid (PNA), although other polynucleotides which minimally interact with the multichromophore in the absence of target can be used in such a format. Alternatively, other embodiments utilize a negatively charged sensor polynucleotide (for example a DNA or RNA probe). Suitable hybridization conditions for a given assay format can be determined by one of skill in the art; nonlimiting parameters which may be adjusted include concentrations of assay components, pH, salts used and their concentration, ionic strength, temperature, etc.

More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing a phosphate or other polyanionic backbone, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms are used interchangeably herein. These terms refer only to the primary structure of the molecule. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, and hybrids thereof including for example hybrids between DNA and RNA, and also include known types of modifications, for example, labels, alkylation, "caps," substitution of one or more of the nucleotides with an analog, internucleotide modifications such as, for example, those with negatively charged linkages (e.g., phosphorothioates, phosphorodithioates, etc.), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

Furthermore, modifications to nucleotidic units include rearranging, appending, substituting for or otherwise altering functional groups on the purine or pyrimidine base which form hydrogen bonds to a respective complementary pyrimidine or purine. The resultant modified nucleotidic unit optionally may form a base pair with other such modified nucleotidic units but not with A, T, C, G or U. Abasic sites may be incorporated which do not prevent the function of the polynucleotide; preferably the polynucleotide does not comprise abasic sites. Some or all of the residues in the polynucleotide can optionally be modified in one or more ways.

Standard A-T and G-C base pairs form under conditions which allow the formation of hydrogen bonds between the N3-H and C4-oxy of thymidine and the N1 and C6-NH2, respectively, of adenosine and between the C2-oxy, N3 and C4-NH2, of cytidine and the C2-NH2, N'—H and C6-oxy, respectively, of guanosine. Thus, for example, guanosine (2-amino-6-oxy-9-β-D-ribofuranosyl-purine) may be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine)

results in a modified nucleotide which will not effectively base pair with guanosine but will form a base pair with isoguanosine. Isocytosine is available from Sigma Chemical Co. (St. Louis, Mo.); isocytidine may be prepared by the method described by Switzer et al. (1993) Biochemistry 32:10489-10496 and references cited therein; 2'-deoxy-5-methyl-isocytidine may be prepared by the method of Tor et al. (1993) J. Am. Chem. Soc. 115:4461-4467 and references cited therein; and isoguanine nucleotides may be prepared using the method described by Switzer et al. (1993), supra, and Mantsch et al. (1993) Biochem. 14:5593-5601, or by the method described in U.S. Pat. No. 5,780,610 to Collins et al. Other normatural base pairs may be synthesized by the method described in Piccirilli et al. (1990) Nature 343:33-37 for the synthesis of 2,6-diaminopyrimidine and its complement (1-methylpyrazolo-[4,3]pyrimidine-5,7-(4H,6H)-dione). Other such modified nucleotidic units which form unique base pairs are known, such as those described in Leach et al. (1992) J. Am. Chem. Soc. 114:3675-3683 and Switzer et al., supra.

"Complementary" or "substantially complementary" refers to the ability to hybridize or base pair between nucleotides or nucleic acids, such as, for instance, between a sensor peptide nucleic acid or polynucleotide and a target polynucleotide. Complementary nucleotides are, generally, A and T (or A and U), or C and G. Two single-stranded polynucleotides or PNAs are said to be substantially complementary when the bases of one strand, optimally aligned and compared and with appropriate insertions or deletions, pair with at least about 80% of the bases of the other strand, usually at least about 90% to 95%, and more preferably from about 98 to 100%.

Alternatively, substantial complementarity exists when a polynucleotide or PNA will hybridize under selective hybridization conditions to its complement. Typically, selective hybridization will occur when there is at least about 65% complementary over a stretch of at least 14 to 25 bases, preferably at least about 75%, more preferably at least about 90% complementary. See, M. Kanehisa Nucleic Acids Res. 12:203 (1984).

"Preferential binding" or "preferential hybridization" refers to the increased propensity of one polynucleotide or PNA to bind to its complement in a sample as compared to a noncomplementary polymer in the sample.

Hybridization conditions will typically include salt concentrations of less than about 1M, more usually less than about 500 mM and preferably less than about 200 mM. In the case of hybridization between a peptide nucleic acid and a polynucleotide, the hybridization can be done in solutions containing little or no salt. Hybridization temperatures can be as low as 5° C., but are typically greater than 22° C., more typically greater than about 30° C., and preferably in excess of about 37° C. Longer fragments may require higher hybridization temperatures for specific hybridization. Other factors may affect the stringency of hybridization, including base composition and length of the complementary strands, presence of organic solvents and extent of base mismatching, and the combination of parameters used is more important than the absolute measure of any one alone. Other hybridization conditions which may be controlled include buffer type and concentration, solution pH, presence and concentration of blocking reagents to decrease background binding such as repeat sequences or blocking protein solutions, detergent type(s) and concentrations, molecules such as polymers which increase the relative concentration of the polynucleotides, metal ion(s) and their concentration(s), chelator(s) and their concentrations, and other conditions known in the art.

"Multiplexing" herein refers to an assay or other analytical method in which multiple analytes can be assayed simultaneously.

"Having" is an open ended phrase like "comprising" and "including," and includes circumstances where additional elements are included and circumstances where they are not.

"Optional" or "optionally" means that the subsequently described event or circumstance may or may not occur, and that the description includes instances where the event or circumstance occurs and instances in which it does not.

The Aggregation Sensor

An aggregation sensor is provided that allows for the detection and analysis of an aggregant. The aggregation sensor comprises a component that can bind to an aggregant or class of aggregants. The interaction may take place through any means known or discoverable in the art. The aggregant and aggregation sensor may form members of a binding pair. The aggregant and aggregation sensor may contain regions of opposite charge that interact electrostatically. The aggregation sensor comprises a larger number of first optically active units having a first absorption wavelength at which they can be excited, and can emit light of a first emission wavelength. The aggregation sensor comprises a lesser number of second optically active units which can absorb light from the excited state of the first optically active units. The aggregation sensor can comprise a ratio of first optically active units to second optically active units of at least three, at least four, at least six, at least nine, or at least nineteen, or more, so long as a sufficient quantity of second optically active units is provided so that energy may be transferred effectively when the sensor is aggregated.

Aggregation thus leads to an increase in energy transfer from the excited state formed by a first optically active unit to the second optically active unit, thereby decreasing the emission from the first optically active unit(s). The second optically active unit may nonradiatively disperse the energy received from the first optically active unit, may emit light of a detectibly different wavelength than the first optically active unit, or may transfer energy to a fluorophore.

Thus aggregation may be assayed by decrease in an emission characteristic of the first optically active unit, by an increase in emission from the second optically active unit(s), or by energy transfer to an additional fluorophore that can absorb energy from the second optically active unit and emit light or transfer energy to a subsequent fluorophore. A quencher may be substituted for a fluorophore at any step in the energy transfer scheme after the first optically active unit where decrease in emission from the first optically active unit is the desired assay format.

Aggregation may result from raising the concentration of the aggregation sensor sufficiently to cause the emission from the first optically active unit to decrease completely, due to effectively all of the first optically active units in the solution being within energy-transferring distance of at least one second optically active unit. When an aggregation sensor is used in solution to analyze a sample for an aggregant, it therefore is used at a concentration where the first optically active unit still shows a detectable emission and energy transfer to the second optically active unit does not account for all energy from the excited state of the first optically active unit.

The large number of individual chromophores within the aggregation sensor (and any aggregate formed) can provide amplification of emission; emission from a fluorophore to which energy is transferred can be more intense when the incident light (the "pump light") is at a wavelength which is absorbed by the aggregation sensor and transferred to the fluorophore than when the fluorophore is directly excited by the pump light.

Each type of optically active unit may comprise one or more subunits capable of absorbing energy. In some embodiments, the optically active units form an excited state and emit light of a characteristic wavelength.

In some embodiments, the aggregation sensors used in the present invention are polycationic so that they can interact with a biomolecule comprising multiple anionic groups, e.g. polysaccharides, polynucleotides, peptides, proteins, etc. In some embodiments, the aggregation sensor can interact with a target polynucleotide electrostatically and thereby bring a signaling chromophore on an uncharged sensor polynucleotide into energy-receiving proximity by virtue of hybridization between the sensor polynucleotide and the target polynucleotide. Any polycationic aggregation sensor that can absorb light and preferably emit or transfer energy can be used in the methods described. Exemplary aggregation sensors that can be used include conjugated polymers, saturated polymers or dendrimers incorporating multiple chromophores in any viable manner, and semiconductor nanocrystals (SCNCs). The conjugated polymers, saturated polymers and dendrimers can be prepared to incorporate multiple cationic species or can be derivatized to render them polycationic after synthesis; semiconductor nanocrystals can be rendered polycationic by addition of cationic species to their surface.

In some embodiments, the aggregation sensor is a conjugated polymer (CP). In some embodiments, the CP is one that comprises "lower bandgap repeat units" of a type and in an amount that contribute a first absorption to the polymer in the range of about 450 nm to about 1000 nm. The lower bandgap repeat units may or may not exhibit such an absorption prior to polymerization, but do introduce that absorption when incorporated into the conjugated polymer. Exemplary absorption ranges include, but are not limited to, wavelengths in the region of 450 nm to 500 nm, 500 nm to 550 nm, 550 nm to 600 nm, 600 nm to 700 nm, and 700 nm to 1000 nm. In certain embodiments the polymer forms an excited state upon contact with incident light having a wavelength including a wavelength of about 488 nm, about 532 nm, about 594 nm and about 633 nm. Additionally, useful incident light wavelengths can include, but are not limited to, 488 nm, 532 nm, 594 nm and 633 nm wavelength light. Such absorption characteristics allow the polymer to be excited at wavelengths that produce less background fluorescence in a variety of settings, including in analyzing biological samples and imaging and/or detecting molecules. Shifting the primary absorbance of the CP to a lower energy and longer wavelength thus can allow for more sensitive and robust methods in certain formats. Additionally, many commercially available instruments incorporate imaging components that operate at such wavelengths at least in part to avoid such issues. For example, thermal cyclers that perform real-time detection during amplification reactions and microarray readers are available which operate in this region. Providing polymers that absorb in this region allows for the adaptation of detection methods to such formats, and also allows entirely new methods to be performed. For use in an aggregation sensor, a second optically active species having or contributing an even lower bandgap absorption is used to receive energy from such a first optically active species, and may be a repeat unit contributing a lower energy absorption to the polymer.

Incorporation of repeat units that decrease the band gap can produce conjugated polymers with such characteristics. Exemplary optionally substituted repeat units which, when incorporated, result in polymers that absorb light at such wavelengths include 2,1,3-benzothiadiazole, benzoselenadiazole, benzotellurodiazole, naphthoselenadiazole, 4,7-di(thien-2-yl)-2,1,3-benzothiadiazole, squaraine dyes, quinoxalines, low bandgap commercial dyes, olefins, and cyano-substituted olefins and isomers thereof. These may be used as the second optically active unit in embodiments of the aggregation sensor.

For example, 2,7-carbazolene-vinylene conjugated polymers have been described with peak absorptions ranging from about 455-485 nm (Morin et al., Chem. Mater. 2004, vol. 16, No. 23, pages 4619-4626). Polymers can be prepared incorporating benzoselenadiazole with absorption maxima at 485 nm. Similarly, polymers incorporating naphthoselenadiazole are known with absorption maxima at 550 nm. Polymers incorporating 4,7-di(thien-2-yl)-2,1,3-benzothiadiazole are known with absorption maxima at about 515 nm. Polymers incorporating cyanovinylenes are known with peak absorptions in this region, for example from 372-537 nm, and exhibiting absorption above 700 nm (PFR(1-4)-S, Macromolecules, Vol. 37, No. 14, pages 5265-5273). Preparation of polymers incorporating repeat units that provide absorption in the spectral region up to 1000 nm has been described (Ajayaghosh, A., et al., Chem. Soc. Rev., 2003, 32, 181; A. Ajayagosh and J. Eldo, Organic Letters, 2001, 3, 2595-2598.) Polymers soluble in polar media and having absorptions from about 450 nm to about 1000 nm can thus be synthesized by incorporation of lower bandgap repeat units and pendant polar or charged groups as described herein.

In some embodiments, the polymer is one whose absorbance is not shifted significantly in the presence of target or anionic polynucleotide. Desirably, the polymer exhibits no more than about a 15 nm shift in peak absorbance in the presence of target or anionic polynucleotide; this corresponds to no more than about a 0.08 eV shift for a peak absorption of 480 nm. The polymer may exhibit a peak absorbance shift of about 20, 15, 12, 10, 8 or 5 nm or less. The polymer may exhibit a peak absorbance shift of about 0.10, 0.08, 0.06, 0.04 eV or less. This stability in absorbance can provide desirable properties in bioassays. Polymers whose absorbance shifts excessively depending on assay conditions can lead to undesirable variability.

In some embodiments, a sufficient amount of an appropriate lower bandgap repeat unit is incorporated into the CP to render it capable of absorbing energy at a desired wavelength above 450 nm and providing a detectable signal, where it is desired that the aggregation sensor be excited in this region.

In some embodiments the polymer can amplify the signal from a fluorophore to which it can transfer energy upon excitation. Desirably, the polymer is of a length and comprises a sufficient amount of repeat units contributing a first absorption wavelength so that upon excitation it transmits sufficient energy to a second or subsequent optically active species (for example another repeat unit contributing a lower energy absorption or a fluorophore) so as to achieve a 50% or greater increase in light emission from the fluorophore than can be achieved by direct excitation of the fluorophore in the absence of polymer. The exact amount of a repeat unit of interest needed to provide the desired degree of amplification is dependent on a number of factors, and may be determined empirically for a given repeat unit. Factors to be considered include the length of the polymer, the molar absorptivity contributed by the repeat unit, and the interaction between the polymer and the aggregant or biomolecule(s) with which it interacts. The polymer can desirably be of a length and comprise a sufficient amount of a repeat units of interest to provide a two-fold, three-fold, four-fold, five-fold, or greater increase in emission from an optically active species to which it can transfer energy.

The CP can be a copolymer, and may be a block copolymer, a graft copolymer, or both. A given repeat unit may be incorporated into the polymer randomly, alternately, periodically and/or in blocks.

The particular size of the polymer is not critical, so long as it is able to absorb light in the relevant region. In some embodiments, the polymer (which includes oligomers) also desirably is able to transfer energy to a fluorophore. In some embodiments the polymer has a molecular mass of at least about 1,000 Daltons to allow for efficient interaction with a biomolecule. Typically the polymer will have a molecular mass of about 250,000 Daltons or less. An oligomer has at least two repeats of a chromophoric unit, and may have a plurality of repeats including 3, 4, 5 or more repeats. An oligomer can also comprise a combination of one or more different chromophoric units, each of which independently may or may not be repeated.

In some embodiments, the polymer may comprise optionally substituted fluorenyl repeat units. Polymers comprising fluorenyl repeat units exhibiting desirable characteristics and are well studied. However, the absorption profile of fluorene repeat units shows absorption at shorter wavelengths than is desired in some embodiments described herein. Thus fluorene copolymers additionally incorporating repeat units with lower bandgaps than fluorene may be desirable in some applications described herein.

In some embodiments, the polymer may comprise optionally substituted biphenylene repeat units. In some embodiments, the polymer may comprise optionally substituted 2,7-carbazolenevinylene repeat units.

The terms "monomer", "monomeric unit" and "repeat unit" are used interchangeably herein to denote conjugated subunits of a polymer or oligomer. It is to be understood that the repeat units can be incorporated into the polymer at any available position(s) and can be substituted with one or more different groups. Exemplary substituents on the repeat units can be selected from alkyl groups, C1-20 alkyl groups optionally substituted at one or more positions with S, N, O, P or Si atoms, C4-16 alkyl carbonyloxy, C4-16 aryl(trialkylsiloxy), alkoxy, C1-20 alkoxy, cyano, C1-20 alkylcarbonyloxy, and C1-20 thioether.

The CP contains a sufficient density of solubilizing functionalities to render the overall polymer soluble in a polar medium. Exemplary polar media include dimethylsulfoxide (DMSO), dimethylformamide (DMF), ethanol, methanol, isopropanol, dioxane, acetone, acetonitrile, 1-methyl-2-pyrrolidinone, formaldehyde, water, and mixtures comprising these solvents. The CP is desirably soluble in at least one of these polar media, and may be soluble in more than one polar media. The CP preferably contains at least about 0.01 mol % of the solubilizing functionality, and may contain at least about 0.02 mol %, at least about 0.05 mol %, at least about 0.1 mol %, at least about 0.2 mol %, at least about 0.5 mol %, at least about 1 mol %, at least about 2 mol %, at least about 5 mol %, at least about 10 mol %, at least about 20 mol %, or at least about 30 mol %. The CP may contain up to 100 mol % of the solubilizing functionality, and may contain about 99 mol % or less, about 90 mol % or less, about 80 mol % or less, about 70 mol % or less, about 60 mol % or less, about 50 mol % or less, or about 40 mol % or less. Where monomers are polysubstituted, the CP may contain 200 mol %, 300 mol %, 400 mol % or more solubilizing functionalities.

The CPs comprise polar groups as solubilizing functionalities linked to polymer subunits to increase polymer solubility in polar media. Any or all of the subunits of the CP may comprise one or more pendant solubilizing groups. Exemplary polar groups include those introducing one or more dipole moments to the CP, for example halides, hydroxyls, amines, amides, cyano, carboxylic acids, and thiols.

In some embodiments, the polar substituents can be charged groups, for example cationic or anionic groups. Any suitable cationic or anionic groups may be incorporated into CPs. When a cationic group is incorporated the polymer is referred to as a cationic conjugated polymer (CCP). Exemplary cationic groups which may be incorporated include ammonium groups, guanidinium groups, histidines, polyamines, pyridinium groups, and sulfonium groups. Exemplary anionic groups include carboxylates, sulfates, and nitrates. The conjugated polymers may have a sufficient density of solubilizing polar groups to render them soluble in a highly polar solvent such as water and/or methanol. This can be particularly advantageous for preparing multilayer polymeric devices via solution processing methods.

The solubilizing functionality may be linked to the conjugated polymer backbone by a linker, preferably an unconjugated linker, for example alkyl groups, polyethers, alkylamines, and/or polyamines.

Desirably, the CPs described herein are soluble in aqueous solutions and other polar solvents, and preferably are soluble in water. By "water-soluble" is meant that the material exhibits solubility in a predominantly aqueous solution, which, although comprising more than 50% by volume of water, does not exclude other substances from that solution, including without limitation buffers, blocking agents, cosolvents, salts, metal ions and detergents.

One synthetic approach to introducing a charged group into a conjugated polymer is as follows. A neutral polymer can be formed by the Suzuki coupling of one or more bis- (or tris-etc.) boronic acid-substituted monomers with one or more monomers that have at least two bromine substitutions on aromatic ring positions. Bromine groups can also be attached to any or all of the monomers via linkers. Polymer ends can be capped by incorporation of a monobrominated aryl group, for example bromobenzene. Conversion of the polymer to a cationic water-soluble form is accomplished by addition of condensed trimethylamine.

In some embodiments, the CCPs comprise one or more angled linkers with a substitution pattern (or regiochemistry) capable of perturbing the polymers' ability to form rigid-rod structures, allowing the CCPs to have a greater range of three-dimensional structures. The angled linker(s) are optionally substituted aromatic molecules having at least two separate bonds to other polymer components (e.g., monomers, block polymers, end groups) that are capable of forming angles relative to one another which disrupt the overall ability of the polymer to form an extended rigid-rod structure (although significant regions exhibiting such structure may remain). The angled linkers may be bivalent or polyvalent.

The angle which the angled linkers are capable of imparting to the polymeric structure is determined as follows. Where the two bonds to other polymeric components are coplanar, the angle can be determined by extending lines representing those bonds to the point at which they intersect, and then measuring the angle between them. Where the two bonds to other polymeric components are not coplanar, the angle can be determined as follows: a first line is drawn between the two ring atoms to which the bonds attach; two bond lines are drawn, one extending from each ring atom in the direction of its respective bond to the other polymeric component to which it is joined; the angle between each bond line and the first line is fixed; and the two ring atoms are then merged into a single point by shrinking the first line to a zero length; the angle then resulting between the two bond lines is the angle the angled linker imparts to the CCP.

The angle which an angled linker is capable of imparting to the polymer is typically less than about 155°, and may be less than about 150°, less than about 145°, less than about 140°, less than about 135°, less than about 130°, less than about 125°, less than about 120°, less than about 115°, less than about 110°, less than about 105°, less than about 100°, less than about 95°, less than about 90°, less than about 85°, less than about 80°, less than about 75°, less than about 70°, less than about 65°, less than about 60°, less than about 55°, or less than about 50°. The angled linker may form an angle to its adjacent polymeric units of about 25°, 30°, 35°, 40°, 45°, 50°, 60° or more. The angled linker may introduce a torsional twist in the conjugated polymer, thereby further disrupting the ability of the polymer to form a rigid-rod structure. For angled linkers having an internally rotatable bond, such as polysubstituted biphenyl, the angled linker must be capable of imparting an angle of less than about 155° in at least one orientation.

For six-membered rings, such angles can be achieved through ortho or meta linkages to the rest of the polymer. For five-membered rings, adjacent linkages fall within this range. For eight-membered rings, linkages extending from adjacent ring atoms, from alternate ring atoms (separated by one ring atom), and from ring atoms separated by two other ring atoms fall within this range. Ring systems with more than eight ring atoms may be used. For polycyclic structures, even more diverse linkage angles can be achieved.

Exemplary linking units which meet these limitations include benzene derivatives incorporated into the polymer in the 1, 2 or 1,3-positions; naphthalene derivatives incorporated into the polymer in the 1,2-, 1,3-, 1,6-, 1,7-, 1,8-positions; anthracene derivatives incorporated into the polymer in the 1,2-, 1,3-, 1,6-, 1,7-, 1,8-, and 1,9-positions; biphenyl derivatives incorporated into the polymer in the 2,3-, 2,4-, 2,6-, 3,3'-, 3,4-, 3,5-, 2,2'-, 2,3'-, 2,4'-, and 3,4'-positions; and corresponding heterocycles. The position numbers are given with reference to unsubstituted carbon-based rings, but the same relative positions of incorporation in the polymer are encompassed in substituted rings and/or heterocycles should their distribution of substituents change the ring numbering.

The CCP may contain at least about 0.01 mol % of the angled linker, at least about 0.02 mol %, at least about 0.05 mol %, at least about 0.1 mol %, at least about 0.2 mol %, at least about 0.5 mol %, at least about 1 mol %, at least about 2 mol %, at least about 5 mol %, at least about 10 mol %, at least about 20 mol %, or at least about 30 mol %. The CCP may contain about 90 mol % or less, about 80 mol % or less, about 70 mol % or less, about 60 mol % or less, about 50 mol % or less, or about 40 mol % or less.

An aggregation sensor may be provided in isolated and/or purified form. Any suitable purification or isolation technique may be used, alone or in combination with any other technique. Exemplary techniques include precipitation, crystallization, sublimation, chromatography, dialysis, extraction, etc.

A Biomolecule Aggregant

An aggregant to be assayed may be a target biomolecule (e.g., a polysaccharide, a polynucleotide, a peptide, a protein, etc.). In some embodiments the target may interact at least in part electrostatically with an aggregation sensor, and may also bind to a sensor biomolecule or probe in some formats. A target polynucleotide may be a particular species of aggregant that is desired to be analyzed, and may be specifically detected using an aggregation sensor and a sensor polynucleotide probe, which may be labeled with a fluorophore as described herein. The target polynucleotide can be single-stranded, double-stranded, or higher order, and can be linear or circular. Exemplary single-stranded target polynucleotides include mRNA, rRNA, tRNA, hnRNA, ssRNA or ssDNA viral genomes, although these polynucleotides may contain internally complementary sequences and significant secondary structure. Exemplary double-stranded target polynucleotides include genomic DNA, mitochondrial DNA, chloroplast DNA, dsRNA or dsDNA viral genomes, plasmids, phage, and viroids. The target polynucleotide can be prepared synthetically or purified from a biological source. The target polynucleotide may be purified to remove or diminish one or more undesired components of the sample or to concentrate the target polynucleotide. Conversely, where the target polynucleotide is too concentrated for the particular assay, the target polynucleotide may be diluted.

Following sample collection and optional nucleic acid extraction, the nucleic acid portion of the sample comprising the target polynucleotide can be subjected to one or more preparative reactions. These preparative reactions can include in vitro transcription (IVT), labeling, fragmentation, amplification and other reactions. mRNA can first be treated with reverse transcriptase and a primer to create cDNA prior to detection and/or amplification; this can be done in vitro with purified mRNA or in situ, e.g. in cells or tissues affixed to a slide. Nucleic acid amplification increases the copy number of sequences of interest such as the target polynucleotide. A variety of amplification methods are suitable for use, including the polymerase chain reaction method (PCR), the ligase chain reaction (LCR), self sustained sequence replication (3SR), nucleic acid sequence-based amplification (NASBA), the use of Q Beta replicase, reverse transcription, nick translation, and the like.

Where the target polynucleotide is single-stranded, the first cycle of amplification forms a primer extension product complementary to the target polynucleotide. If the target polynucleotide is single-stranded RNA, a polymerase with reverse transcriptase activity is used in the first amplification to reverse transcribe the RNA to DNA, and additional amplification cycles can be performed to copy the primer extension products. The primers for a PCR must, of course, be designed to hybridize to regions in their corresponding template that will produce an amplifiable segment; thus, each primer must hybridize so that its 3' nucleotide is paired to a nucleotide in its complementary template strand that is located 3' from the 3' nucleotide of the primer used to replicate that complementary template strand in the PCR.

The target polynucleotide can be amplified by contacting one or more strands of the target polynucleotide with a primer and a polymerase having suitable activity to extend the primer and copy the target polynucleotide to produce a full-length complementary polynucleotide or a smaller portion thereof. Any enzyme having a polymerase activity that can copy the target polynucleotide can be used, including DNA polymerases, RNA polymerases, reverse transcriptases, enzymes having more than one type of polymerase activity, and the enzyme can be thermolabile or thermostable. Mixtures of enzymes can also be used. Exemplary enzymes include: DNA polymerases such as DNA Polymerase I ("Pol I"), the Klenow fragment of Pol I, T4, T7, Sequenase® T7, Sequenase® Version 2.0 T7, Tub, Taq, Tth, Pfx, Pfu, Tsp, Tfl, Tli and *Pyrococcus* sp GB-D DNA polymerases; RNA polymerases such as *E. coli*, SP6, T3 and T7 RNA polymerases; and reverse transcriptases such as AMV, M-MuLV, MMLV, RNAse H⁻ MMLV (SuperScript®), SuperScript® II, ThermoScript®, HIV-1, and RAV2 reverse transcriptases. All of these enzymes are commercially available. Exemplary polymerases with multiple specificities include RAV2 and Tli (exo-) polymerases. Exemplary thermostable polymerases include Tub, Taq, Tth, Pfx, Pfu, Tsp, Tfl, Tli and *Pyrococcus* sp. GB-D DNA polymerases.

Suitable reaction conditions are chosen to permit amplification of the target polynucleotide, including pH, buffer, ionic strength, presence and concentration of one or more salts, presence and concentration of reactants and cofactors such as nucleotides and magnesium and/or other metal ions (e.g., manganese), optional cosolvents, temperature, thermal cycling profile for amplification schemes comprising a polymerase chain reaction, and may depend in part on the polymerase being used as well as the nature of the sample. Cosolvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot-start techniques, use of nested primers, or designing PCR primers so that they form stem-loop structures in the event of primer-dimer formation and thus are not amplified. Techniques to accelerate PCR can be used, for example centrifugal PCR, which allows for greater convection within the sample, and comprising infrared heating steps for rapid heating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different target polynucleotides or different regions of a particular target polynucleotide within the sample.

Amplified target polynucleotides may be subjected to post amplification treatments. For example, in some cases, it may be desirable to fragment the target polynucleotide prior to hybridization in order to provide segments which are more readily accessible. Fragmentation of the nucleic acids can be carried out by any method producing fragments of a size useful in the assay being performed; suitable physical, chemical and enzymatic methods are known in the art.

An amplification reaction can be performed under conditions which allow the sensor polynucleotide to hybridize to the amplification product during at least part of an amplification cycle. When the assay is performed in this manner, real-time detection of this hybridization event can take place by monitoring for light emission during amplification.

Real time PCR product analysis (and related real time reverse-transcription PCR) provides a known technique for real time PCR monitoring that has been used in a variety of contexts, which can be adapted for use with the methods described herein (see, Laurendeau et al. (1999) "TaqMan PCR-based gene dosage assay for predictive testing in individuals from a cancer family with INK4 locus haploinsufficiency" Clin Chem 45(7):982-6; Laurendeau et al. (1999) "Quantitation of MYC gene expression in sporadic breast tumors with a real-time reverse transcription-PCR assay" Clin Chem 59(12):2759-65; and Kreuzer et al. (1999) "Light-Cycler technology for the quantitation of bcr/abl fusion transcripts" Cancer Research 59(13):3171-4).

The Sample

In principle, the sample can be any material suspected of containing an aggregant capable of causing aggregation of the aggregation sensor. In some embodiments, the sample can be any source of biological material which comprises a biomolecule, for example a polynucleotide, that can be obtained from a living organism directly or indirectly, including cells, tissue or fluid, and the deposits left by that organism, including viruses, mycoplasma, and fossils. The sample may comprise an aggregant prepared through synthetic means, in whole or in part. Typically, the sample is obtained as or dispersed in a predominantly aqueous medium. Nonlimiting examples of the sample include blood, urine, semen, milk, sputum, mucus, a buccal swab, a vaginal swab, a rectal swab, an aspirate, a needle biopsy, a section of tissue obtained for example by surgery or autopsy, plasma, serum, spinal fluid, lymph fluid, the external secretions of the skin, respiratory, intestinal, and genitourinary tracts, tears, saliva, tumors, organs, samples of in vitro cell culture constituents (including but not limited to conditioned medium resulting from the growth of cells in cell culture medium, putatively virally infected cells, recombinant cells, and cell components), and a recombinant library comprising polynucleotide sequences.

The sample can be a positive control sample which is known to contain the aggregant or a surrogate therefor. A negative control sample can also be used which, although not expected to contain the aggregant, is suspected of containing it (via contamination of one or more of the reagents) or another component capable of producing a false positive, and is tested in order to confirm the lack of contamination by the aggregant of the reagents used in a given assay, as well as to determine whether a given set of assay conditions produces false positives (a positive signal even in the absence of aggregant in the sample).

The sample can be diluted, dissolved, suspended, extracted or otherwise treated to solubilize and/or purify an aggregant present or to render it accessible to reagents. any target polynucleotide which are used in an amplification scheme or to detection reagents. Where the sample contains cells, the cells can be lysed or permeabilized to release an aggregant of interest within the cells. One step permeabilization buffers can be used to lyse cells which allow further steps to be performed directly after lysis, for example a polymerase chain reaction.

The Probe

One or more probes may be employed that bind to particular species of aggregants. The probe and the aggregant may form a binding pair that specifically bind to each other even with an aggregate. The probe can comprise a fluorophore or quencher that can participate in energy transfer schemes useful for methods as described herein.

A sensor biomolecule can be used as a probe that can bind to a target biomolecule. Exemplary biomolecules include polysaccharides, polynucleotides, peptides, proteins, etc. The sensor biomolecule can be conjugated to a substrate. The sensor may also interact at least in part electrostatically with a polycationic multichromophore, which may be a conjugated polymer. The sensor biomolecule, the target biomolecule, and the aggregation sensor when bound together form a detection complex, a form of the aggregant comprising the sensor and aggregant. In some embodiments, a sensor polynucleotide is provided that is complementary to a target polynucleotide to be assayed, and which does not interact with the aggregation sensor in the absence of target to a degree that precludes the detection of target using the described techniques. Desirably, in some embodiments, the sensor lacks a polyanionic backbone as found in RNA and DNA.

A sensor polynucleotide can be branched, multimeric or circular, but is typically linear, and can contain normatural bases. The sensor may be labeled or unlabeled with a detectable moiety.

In some embodiments, the sensor is desirably unlabelled with a moiety that absorbs energy from the aggregation sensor; particularly, the sensor is unlabelled with a fluorophore or quencher that absorbs energy from an excited state of the aggregation sensor.

In some embodiments a sensor polynucleotide is labeled with a fluorophore that can absorb energy from the aggregation sensor and be used in a fluorescence transfer method for detection of polyanionic species.

The sensor may be a PNA, the molecular structures of which are well known. PNAs can be prepared with any desired sequence of bases. Specific sensor PNA structures can be custom-made using commercial sources or chemically synthesized.

Fluorophores

In some embodiments, a fluorophore may be employed, for example to receive energy transferred from an excited state of an optically active unit, or to exchange energy with a labeled probe, or in multiple energy transfer schemes. Fluorophores useful in the inventions described herein include any substance which can absorb energy of an appropriate wavelength and emit or transfer energy. For multiplexed assays, a plurality of different fluorophores can be used with detectably different emission spectra. Typical fluorophores include fluorescent dyes, semiconductor nanocrystals, lanthanide chelates, and green fluorescent protein.

Exemplary fluorescent dyes include fluorescein, 6-FAM, rhodamine, Texas Red, tetramethylrhodamine, a carboxyrhodamine, carboxyrhodamine 6G, carboxyrhodol, carboxyrhodamine 110, Cascade Blue, Cascade Yellow, coumarin, Cy2®, Cy3®, Cy3.5®, Cy5®, Cy5.5®, Cy-Chrome, phycoerythrin, PerCP (peridinin chlorophyll-a Protein), PerCP-Cy5.5, JOE (6-carboxy-4',5'-dichloro-2',7'-dimethoxyfluorescein), NED, ROX (5-(and-6)-carboxy-X-rhodamine), HEX, Lucifer Yellow, Marina Blue, Oregon Green 488, Oregon Green 500, Oregon Green 514, Alexa Fluor® 350, Alexa Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-amino-4-methylcoumarin-3-acetic acid, BODIPY® FL, BODIPY® FL-Br$_2$, BODIPY® 530/550, BODIPY® 558/568, BODIPY® 564/570, BODIPY® 576/589, BODIPY® 581/591, BODIPY® 630/650, BODIPY® 650/665, BODIPY® R6G, BODIPY® TMR, BODIPY® TR, conjugates thereof, and combinations thereof. Exemplary lanthanide chelates include europium chelates, terbium chelates and samarium chelates.

A wide variety of fluorescent semiconductor nanocrystals ("SCNCs") are known in the art; methods of producing and utilizing semiconductor nanocrystals are described in: PCT Publ. No. WO 99/26299 published May 27, 1999, inventors Bawendi et al.; U.S. Pat. No. 5,990,479 issued Nov. 23, 1999 to Weiss et al.; and Bruchez et al., Science 281:2013, 1998. Semiconductor nanocrystals can be obtained with very narrow emission bands with well-defined peak emission wavelengths, allowing for a large number of different SCNCs to be used as signaling chromophores in the same assay, optionally in combination with other non-SCNC types of signaling chromophores.

Exemplary polynucleotide-specific dyes include acridine orange, acridine homodimer, actinomycin D, 7-aminoactinomycin D (7-AAD), 9-amino-6-chloro-2-methoxyacridine (ACMA), BOBO™-1 iodide (462/481), BOBO™-3 iodide (570/602), BO-PRO™-1 iodide (462/481), BO-PRO™-3 iodide (575/599), 4',6-diamidino-2-phenylindole, dihydrochloride (DAPI), 4',6-diamidino-2-phenylindole, dihydrochloride (DAPI), 4',6-diamidino-2-phenylindole, dilactate (DAPI, dilactate), dihydroethidium (hydroethidine), dihydroethidium (hydroethidine), dihydroethidium (hydroethidine), ethidium bromide, ethidium diazide chloride, ethidium homodimer-1 (EthD-1), ethidium homodimer-2 (EthD-2), ethidium monoazide bromide (EMA), hexidium iodide, Hoechst 33258, Hoechst 33342, Hoechst 34580, Hoechst 5769121, hydroxystilbamidine, methanesulfonate, JOJO™-1 iodide (529/545), JO-PRO™-1 iodide (530/546), LOLO™-1 iodide (565/579), LO-PRO™-1 iodide (567/580), NeuroTrace™ 435/455, NeuroTrace™ 500/525, NeuroTrace™ 515/535, NeuroTrace™ 530/615, NeuroTrace™ 640/660, OliGreen, PicoGreen® ssDNA, PicoGreen® dsDNA, POPO™-1 iodide (434/456), POPO™-3 iodide (534/570), PO-PRO™-1 iodide (435/455), PO-PRO™-3 iodide (539/567), propidium iodide, RiboGreen®, SlowFade®, SlowFade® Light, SYBR® Green I, SYBR® Green II, SYBR® Gold, SYBR® 101, SYBR® 102, SYBR® 103, SYBR® DX, TO-PRO®-1, TO-PRO®-3, TO-PRO®-5, TOTO®-1, TOTO®-3, YO-PRO®-1 (oxazole yellow), YO-PRO®-3, YOYO®-1, YOYO®-3, TO, SYTOX® Blue, SYTOX® Green, SYTOX® Orange, SYTO® 9, SYTO® BC, SYTO® 40, SYTO® 41, SYTO® 42, SYTO® 43, SYTO® 44, SYTO® 45, SYTO® Blue, SYTO® 11, SYTO® 12, SYTO® 13, SYTO® 14, SYTO® 15, SYTO® 16, SYTO® 20, SYTO® 21, SYTO® 22, SYTO® 23, SYTO® 24, SYTO® 25, SYTO® Green, SYTO® 80, SYTO® 81, SYTO® 82, SYTO® 83, SYTO® 84, SYTO® 85, SYTO® Orange, SYTO® 17, SYTO® 59, SYTO® 60, SYTO® 61, SYTO® 62, SYTO® 63, SYTO® 64, SYTO® Red, netropsin, distamycin, acridine orange, 3,4-benzopyrene, thiazole orange, TOMEHE, daunomycin, acridine, pentyl-TOTAB, and butyl-TOTIN. Asymmetric cyanine dyes may be used as the polynucleotide-specific dye. Other dyes of interest include those described by Geierstanger, B. H. and Wemmer, D. E., Annu. Rev. Vioshys. Biomol. Struct. 1995, 24, 463-493, by Larson, C. J. and Verdine, G. L., Bioorganic Chemistry: Nucleic Acids, Hecht, S. M., Ed., Oxford University Press: New York, 1996; pp 324-346, and by Glumoff, T. and Goldman, A. Nucleic Acids in Chemistry and Biology, 2$^{nd}$ ed., Blackburn, G. M. and Gait, M. J., Eds., Oxford University Press: Oxford, 1996, pp 375-441. The polynucleotide-specific dye may be an intercalating dye, and may be specific for double-stranded polynucleotides. Other dyes and fluorophores are described at www.probes.com (Molecular Probes, Inc.).

The term "green fluorescent protein" refers to both native *Aequorea* green fluorescent protein and mutated versions that have been identified as exhibiting altered fluorescence characteristics, including altered excitation and emission maxima, as well as excitation and emission spectra of different shapes (Delagrave, S. et al. (1995) Bio/Technology 13:151-154; Heim, R. et al. (1994) Proc. Natl. Acad. Sci. USA 91:12501-12504; Heim, R. et al. (1995) Nature 373: 663-664). Delgrave et al. isolated mutants of cloned *Aequorea victoria* GFP that had red-shifted excitation spectra. Bio/Technology 13:151-154 (1995). Heim, R. et al. reported a mutant (Tyr66 to His) having a blue fluorescence (Proc. Natl. Acad. Sci. (1994) USA 91:12501-12504).

The Substrate

In some embodiments, an assay component can be located upon a substrate. The substrate can comprise a wide range of material, either biological, nonbiological, organic, inorganic, or a combination of any of these. For example, the substrate may be a polymerized Langmuir Blodgett film, functionalized glass, Si, Ge, GaAs, GaP, SiO$_2$, SiN$_4$, modified silicon, or any one of a wide variety of gels or polymers such as (poly) tetrafluoroethylene, (poly)vinylidenedifluoride, polystyrene, cross-linked polystyrene, polyacrylic, polylactic acid, polyglycolic acid, poly(lactide coglycolide), polyanhydrides, poly (methyl methacrylate), poly(ethylene-co-vinyl acetate), polysiloxanes, polymeric silica, latexes, dextran polymers, epoxies, polycarbonates, or combinations thereof. Conducting polymers and photoconductive materials can be used.

Substrates can be planar crystalline substrates such as silica based substrates (e.g. glass, quartz, or the like), or crystalline substrates used in, e.g., the semiconductor and microprocessor industries, such as silicon, gallium arsenide, indium doped GaN and the like, and includes semiconductor nanocrystals.

The substrate can take the form of a photodiode, an optoelectronic sensor such as an optoelectronic semiconductor chip or optoelectronic thin-film semiconductor, or a biochip. The location(s) of probe(s) on the substrate can be addressable; this can be done in highly dense formats, and the location(s) can be microaddressable or nanoaddressable.

Silica aerogels can also be used as substrates, and can be prepared by methods known in the art. Aerogel substrates may be used as free standing substrates or as a surface coating for another substrate material.

The substrate can take any form and typically is a plate, slide, bead, pellet, disk, particle, microparticle, nanoparticle, strand, precipitate, optionally porous gel, sheets, tube, sphere, container, capillary, pad, slice, film, chip, multiwell plate or dish, optical fiber, etc. The substrate can be any form that is rigid or semi-rigid. The substrate may contain raised or depressed regions on which an assay component is located. The surface of the substrate can be etched using well known techniques to provide for desired surface features, for example trenches, v-grooves, mesa structures, or the like.

Surfaces on the substrate can be composed of the same material as the substrate or can be made from a different material, and can be coupled to the substrate by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed substrate materials. The surface can be optically transparent and can have surface Si—OH functionalities, such as those found on silica surfaces.

The substrate and/or its optional surface can be chosen to provide appropriate characteristics for the synthetic and/or detection methods used. The substrate and/or surface can be transparent to allow the exposure of the substrate by light applied from multiple directions. The substrate and/or surface may be provided with reflective "mirror" structures to increase the recovery of light.

The substrate and/or its surface is generally resistant to, or is treated to resist, the conditions to which it is to be exposed in use, and can be optionally treated to remove any resistant material after exposure to such conditions.

Polynucleotide probes can be fabricated on or attached to the substrate by any suitable method, for example the methods described in U.S. Pat. No. 5,143,854, PCT Publ. No. WO 92/10092, U.S. patent application Ser. No. 07/624,120, filed Dec. 6, 1990 (now abandoned), Fodor et al., Science, 251: 767-777 (1991), and PCT Publ. No. WO 90/15070). Techniques for the synthesis of these arrays using mechanical synthesis strategies are described in, e.g., PCT Publication No. WO 93/09668 and U.S. Pat. No. 5,384,261.

Still further techniques include bead based techniques such as those described in PCT Appl. No. PCT/US93/04145 and pin based methods such as those described in U.S. Pat. No. 5,288,514.

Additional flow channel or spotting methods applicable to attachment of sensor polynucleotides to the substrate are described in U.S. patent application Ser. No. 07/980,523, filed Nov. 20, 1992, and U.S. Pat. No. 5,384,261. Reagents are delivered to the substrate by either (1) flowing within a channel defined on predefined regions or (2) "spotting" on predefined regions. A protective coating such as a hydrophilic or hydrophobic coating (depending upon the nature of the solvent) can be used over portions of the substrate to be protected, sometimes in combination with materials that facilitate wetting by the reactant solution in other regions. In this manner, the flowing solutions are further prevented from passing outside of their designated flow paths.

Typical dispensers include a micropipette optionally robotically controlled, an ink-jet printer, a series of tubes, a manifold, an array of pipettes, or the like so that various reagents can be delivered to the reaction regions sequentially or simultaneously.

The substrate or a region thereof may be encoded so that the identity of the sensor located in the substrate or region being queried may be determined. Any suitable coding scheme can be used, for example optical codes, RFID tags, magnetic codes, physical codes, fluorescent codes, and combinations of codes.

Excitation and Detection

Any instrument that provides a wavelength that can excite the aggregation sensor and is shorter than the emission wavelength(s) to be detected can be used for excitation. Commercially available devices can provide suitable excitation wavelengths as well as suitable detection components.

Exemplary excitation sources include a broadband UV light source such as a deuterium lamp with an appropriate filter, the output of a white light source such as a xenon lamp or a deuterium lamp after passing through a monochromator to extract out the desired wavelengths, a continuous wave (cw) gas laser, a solid state diode laser, or any of the pulsed lasers. Emitted light can be detected through any suitable device or technique; many suitable approaches are known in the art. For example, a fluorimeter or spectrophotometer may be used to detect whether the test sample emits light of a wavelength characteristic of the signaling chromophore upon excitation of the multichromophore.

Incident light wavelengths useful for excitation of aggregation sensors including a plurality of lower bandgap repeat units can include 450 nm to 1000 nm wavelength light.

Exemplary useful incident light wavelengths include, but are not limited to, wavelengths of at least about 450, 500, 550, 600, 700, 800 or 900 nm, and may be less than about 1000, 900, 800, 700, 600, 550 or 500 nm. Exemplary useful incident light in the region of 450 nm to 500 nm, 500 nm to 550 nm, 550 nm to 600 nm, 600 nm to 700 nm, and 700 nm to 1000 nm. In certain embodiments the aggregation sensor forms an excited state upon contact with incident light having a wavelength including a wavelength of about 488 nm, about 532 nm, about 594 nm and/or about 633 nm. Additionally, useful incident light wavelengths can include, but are not limited to, 488 nm, 532 nm, 594 nm and 633 nm wavelength light.

Compositions of Matter

Also provided are compositions of matter of any of the molecules described herein in any of various forms. The aggregation sensors described herein may be provided in purified and/or isolated form. The aggregation sensors may be provided in crystalline form.

The aggregation sensors may be provided in solution, which may be a predominantly aqueous solution, which may comprise one or more of the additional solution components described herein, including without limitation additional solvents, buffers, biomolecules, polynucleotides, fluorophores, etc. The aggregation sensor can be present in solution at a concentration at which a first emission from the first optically active units can be detected in the absence of an aggregant. The solution may comprise additional components as described herein, including labeled probes such as fluorescently labeled polynucleotides, specific for a species of a class of aggregants for the aggregation sensor.

The aggregation sensors may be provided in the form of a film. The compositions of matter may be claimed by any property described herein, including by proposed structure, by method of synthesis, by absorption and/or emission spectrum, by elemental analysis, by NMR spectra, or by any other property or characteristic.

Methods of Use

The aggregation sensors provided herein may be employed in a variety of biological assays. They may be used to detect the presence of an aggregant in a sample, for example a polynucleotide or other biomolecule, and may be used to quantitate the aggregant. In some embodiments, the aggregation sensors bind at least in part electrostatically to a target biomolecule. The target biomolecule may be labeled or unlabeled. One or more assay components (e.g., probe, aggregation sensor, aggregant) may be bound to a substrate.

The novel aggregation sensors may also be used in biological assays in which energy is transferred between one or more of the aggregation sensor, a label on a target aggregant, a label on a probe, and/or a fluorescent dye specific for a polynucleotide, in all permutations. The aggregation sensor may interact at least in part electrostatically with the sensor and/or the target to form additional complexes, and an increase in energy transfer with the aggregation sensor may occur upon binding of the sensor and the target. This method may also be performed on a substrate.

Other variations of such methods are described further herein. Addition of organic solvents in some cases can result in a decrease in background emission by inhibiting nonionic interactions between assay components, for example between the aggregation sensor and a sensor polynucleotide. The added solvent may be a polar organic solvent, and may be water miscible, for example an alcohol such as methanol, ethanol, propanol or isopropanol. The added solvent may be one that does not adversely affect the ability of the sensor to hybridize to the target in the solution, for example 1-methyl-2-pyrrolidinone. The organic solvent may be added in an amount of about 1%, about 2%, about 5%, about 10%, or more of the total solution, and typically is used within the range of about 0.5-10%. Other components may be incorporated into the assay solution, for example one or more buffers suitable for maintaining a pH satisfactory for the biological molecules and their desired properties (e.g., ability to hybridize).

In one variation a plurality of fluorophores, which may be directly or indirectly attached or recruited to any other of the assay components and/or to a substrate, can be used to exchange energy in an energy transfer scheme. In particular applications, this can provide for significant additional selectivity. For example, a polynucleotide-specific dye can be used as an optically active unit, and may be specific for double-stranded sequences. Energy can be transferred to or from an excited aggregation sensor in certain embodiments. The cascade of energy transfer can, in principle, be extended to use any number of optically active units with compatible absorption and emission profiles. In one embodiment of this variation, an intercalating dye that is specific for double-stranded polynucleotides is used. The intercalating dye provides the added selective requirement that the sensor and target polynucleotides hybridize before it is recruited to the detection complex. In the presence of target, the duplex is formed, the dye is recruited, and excitation to or from the dye can occur. In certain embodiments the methods of using intercalating dye(s) can include steps wherein the intercalating dye(s) is in a solution.

In one embodiment a single nucleotide polymorphism (SNP) is detected in an aggregant.

In another embodiment expression of a gene is detected in an aggregant. In a further embodiment, a measured result of detecting an aggregant can be used to diagnose a disease state of a patient. In yet another embodiment the detection method of the invention can further include a method of diagnosing a disease state. In a related embodiment, the method of diagnosing a disease can include reviewing or analyzing data relating to the presence of an aggregant and providing a conclusion to a patient, a health care provider or a health care manager, the conclusion being based on the review or analysis of data regarding a disease diagnosis. Reviewing or analyzing such data can be facilitated using a computer or other digital device and a network as described herein. It is envisioned that information relating to such data can be transmitted over the network.

In practicing the methods of the present invention, known molecular biology techniques are optionally utilized. Exemplary molecular biology techniques are explained in, for example, Ausubel et al. (Eds.) Current Protocols in Molecular Biology, Volumes I, II, and III, (1997), Ausubel et al. (Eds.), Short Protocols in Molecular Biology: A Compendium of Methods from Current Protocols in Molecular Biology, 5$^{th}$ Ed., John Wiley & Sons, Inc. (2002), Sambrook et al., Molecular Cloning: A Laboratory Manual, 3rd Ed., Cold Spring Harbor Laboratory Press (2000), and Innis et al. (Eds.) PCR Protocols: A Guide to Methods and Applications, Elsevier Science & Technology Books (1990).

Any effective detection method can be used in the various methods described herein, including optical, spectroscopic, electrical, electrochemical, piezoelectrical, magnetic, Raman scattering, surface plasmon resonance, radiographic, colorimetric, calorimetric, etc. Preferably the sensor is or can be rendered optically detectable to a human and/or a detection device.

The methods described herein may be used with and incorporated into an apparatus. The methods may be used in conjunction with a commercially available device. Exemplary commercially available systems and instruments that can be used in conjunction with an invention disclosed herein include: array systems such as the Affymetrix Genechip® system, Agilent GenePix® Microarray Scanner, Genomic Solutions GeneMachine®, Asper Biotech Genorama™ Quattroimager, and the Bio-Rad VersArray® ChipReader; and real time PCR systems such as the Applied Biosystems 7900HT Fast Real-Time PCR System, ABI PRISM® 7000 Sequence Detection System, Applied Biosystems 7500 Real-Time PCR System, Applied Biosystems 7300 Real-Time PCR System, Applied Biosystems PRISM® 7700, Bio-Rad MyiQ Single-Color Real-Time PCR Detection System, and the Bio-Rad iCycler iQ Real-Time PCR Detection System.

Articles of Manufacture

For the embodiments of the aggregation sensor that are conjugated polymers (CPs), those polymers can be incorporated into any article of manufacture in which conjugated polymers find use. Exemplary articles of manufacture into which the CPs can be incorporated include optoelectronic or electronic devices, biosensors, diodes, including photodiodes and light-emitting diodes ("LEDs"), optoelectronic semiconductor chips, semiconductor thin-films, and chips, and can be used in array or microarray form. The CPs can be incorporated into a polymeric photoswitch. The CPs can be incorporated into an optical interconnect or a transducer to convert a light signal to an electrical impulse. The CPs can serve as liquid crystal materials. The CPs may be used as electrodes in electrochemical cells, as conductive layers in electrochromic displays, as field effective transistors, and as Schottky diodes.

The CPs can be used as lasing materials. Optically pumped laser emission has been reported from MEH-PPV in dilute solution in an appropriate solvent, in direct analogy with conventional dye lasers [D. Moses, Appl. Phys. Lett. 60, 3215 (1992); U.S. Pat. No. 5,237,582]. Semiconducting polymers in the form of neat undiluted films have been demonstrated as active luminescent materials in solid state lasers [F. Hide, M. A. Diaz-Garcia, B. J. Schwartz, M. R. Andersson, Q. Pei, and A. J. Heeger, Science 273, 1833 (1996); N. Tessler, G. J. Denton, and R. H. Friend, Nature 382, 695 (1996)]. The use of semiconducting polymers as materials for solid state lasers is disclosed in U.S. Pat. No. 5,881,083 issued Mar. 9, 1999 to Diaz-Garcia et al. and titled "Conjugated Polymers as Materials for Solid State Lasers." In semiconducting polymers, the emission is at longer wavelengths than the onset of significant absorption (the Stokes shift) resulting from inter- and intramolecular energy transfer. Thus there is minimal self-absorption of the emitted radiation [F. Hide et al., Science 273, 1833 (1996)], so self-absorption does not make the materials lossy. Moreover, since the absorption and emission are spectrally separated, pumping the excited state via the $\pi$ to $\pi^*$ transition does not stimulate emission, and an inverted population can be obtained at relatively low pump power.

Light-emitting diodes can be fabricated incorporating one or more layers of CPs, described herein which may serve as conductive layers. Light can be emitted in various ways, e.g., by using one or more transparent or semitransparent electrodes, thereby allowing generated light to exit from the device.

The mechanism of operation of a polymer LED requires that carrier injection be optimized and balanced by matching the electrodes to the electronic structure of the semiconducting polymer. For optimum injection, the work function of the anode should lie at approximately the top of the valence band, $E_v$, (the $\pi$-band or highest occupied molecular orbital, HOMO) and the work function of the cathode should lie at approximately the bottom of the conduction band, $E_c$, (the $\pi^*$-band or lowest unoccupied molecular orbital, LUMO).

LED embodiments include hole-injecting and electron-injecting electrodes. A conductive layer made of a high work function material (above 4.5 eV) may be used as the hole-injecting electrode. Exemplary high work function materials include electronegative metals such as gold or silver, and metal-metal oxide mixtures such as indium-tin oxide. An electron-injecting electrode can be fabricated from a low work function metal or alloy, typically having a work function below 4.3. Exemplary low work function materials include indium, calcium, barium and magnesium. The electrodes can be applied by any suitable method; a number of methods are known to the art (e.g. evaporated, sputtered, or electron-beam evaporation).

In some embodiments, polymer light-emitting diodes can be fabricated using a semiconducting polymer cast from solution in an organic solvent as an emissive layer and a water-soluble (or methanol-soluble) conjugated copolymer as an electron-transport layer (ETL) in the device configuration: ITO(indium tin oxide)/PEDOT(poly(3,4-ethylene dioxythiophene)/emissive polymer/ETL/Ba/Al.

Any form of conducting layer can be used. Thus, judicious choice of monomers as described herein can result in polymers with hole-injecting and/or transporting properties, as well as polymers with electron-injecting and/or transporting properties. The device geometry and deposition order can be selected based on the type of conductive polymer being used. More than one type of conductive polymer can be used in the same multilayer device. A multilayer device may include more than one layer of electron-injecting conjugated polymers, more than one layer of hole-injecting conjugated polymers, or at least one layer of a hole-injecting polymer and at least one layer of an electron-injecting conjugated polymer.

In PLEDs, the device efficiency is reduced by cathode quenching since the recombination zone is typically located near the cathode.[20] The addition of an ETL moves the recombination zone away from the cathode and thereby eliminates cathode quenching. In addition, the ETL can serve to block the diffusion of metal atoms, such as barium and calcium, and thereby prevents the generation of quenching centers[20] during the cathode deposition process.

In some embodiments, the principal criteria when a soluble conjugated polymer is used as an electron transport layer (ETL) in polymer light-emitting diodes (PLEDs) are the following: (1) The lowest unoccupied molecular orbital (LUMO) of the ETL must be at an energy close to, or even within the $\pi^*$-band of the emissive semiconducting polymer (so electrons can be injected); and (2) The solvent used for casting the electron injection material must not dissolve the underlying emissive polymer.

Figure 4:
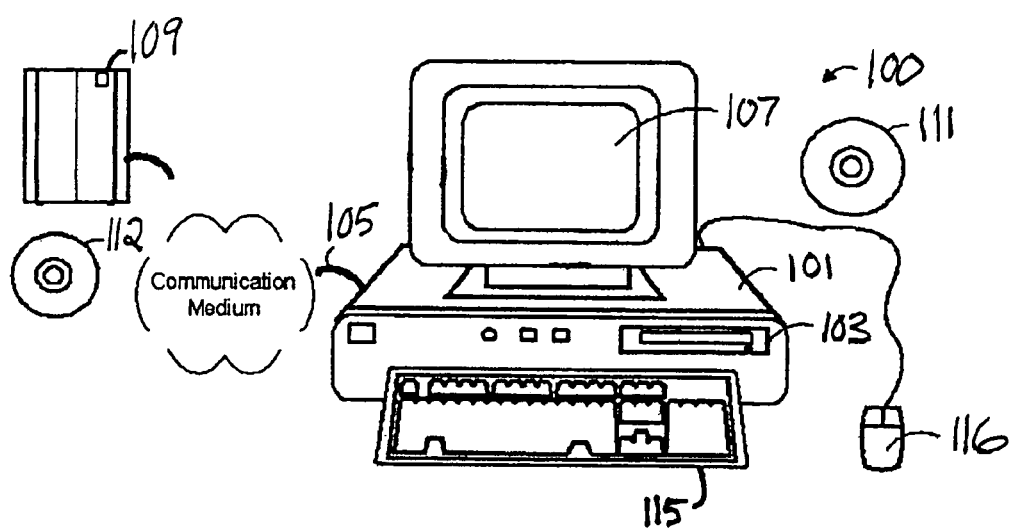
FIG. 4. Block diagram showing a representative example logic device.

FIG. 4 is a block diagram showing a representative example logic device through which reviewing or analyzing data relating to the present invention can be achieved. Such data can be in relation to a disease, disorder or condition in a subject. FIG. 4 shows a computer system (or digital device) 100 that may be understood as a logical apparatus that can read instructions from media 111 and/or network port 105, which can optionally be connected to server 109 having fixed media 112. The system shown in FIG. 4 includes CPU 101, disk drives 103, optional input devices such as keyboard 115 and/or mouse 116 and optional monitor 107. Data communication can be achieved through the indicated communication medium to a server 109 at a local or a remote location. The communication medium can include any means of transmitting and/or receiving data. For example, the communication medium can be a network connection, a wireless connection or an internet connection. It is envisioned that data relating to the present invention can be transmitted over such networks or connections.

In one embodiment, a computer-readable medium includes a medium suitable for transmission of a result of an analysis of a biological sample. The medium can include a result regarding a disease condition or state of a subject, wherein such a result is derived using the methods described herein.

Similarly, the principal criteria for a polymer based hole transport layer (HTL) for use in polymer light-emitting diodes (PLEDs) is that the highest occupied molecular orbital (HOMO) of the HTL must be at an energy close to, or even within the valence band of the emissive semiconducting polymer.

Solubility considerations can dictate the deposition order of the particular CPs and solvents used to produce a desired device configuration. Any number of layers of CPs with different solubilities may be deposited via solution processing by employing these techniques.

The PLEDs comprising CPs described herein can be incorporated in any available display device, including a full color LED display, a cell phone display, a PDA (personal digital assistant), portable combination devices performing multiple functions (phone/PDA/camera/etc.), a flat panel display including a television or a monitor, a computer monitor, a laptop computer, a computer notepad, and an integrated computer-monitor systems. The PLEDs may be incorporated in active or passive matrices.

Kits

Kits comprising reagents useful for performing described methods are also provided.

In some embodiments, a kit comprises an aggregation sensor as described herein and one or more fluorescently labeled probes specific for a species of aggregant of interest. In the presence of the specific aggregant in the sample, the sensor is brought into proximity to the aggregation sensor via binding to the aggregant.

The kit may optionally contain one or more of the following: one or more labels that can be incorporated into an aggregant; one or more intercalating dyes; one or more sensor biomolecules, one or more substrates which may or may not contain an array, etc.

The components of a kit can be retained by a housing. Instructions for using the kit to perform a described method can be provided with the housing, and can be provided in any fixed medium. The instructions may be located inside the housing or outside the housing, and may be printed on the interior or exterior of any surface forming the housing that renders the instructions legible. A kit may be in multiplex form for detection of one or more different target polynucleotides or other biomolecules.

Figure 5:
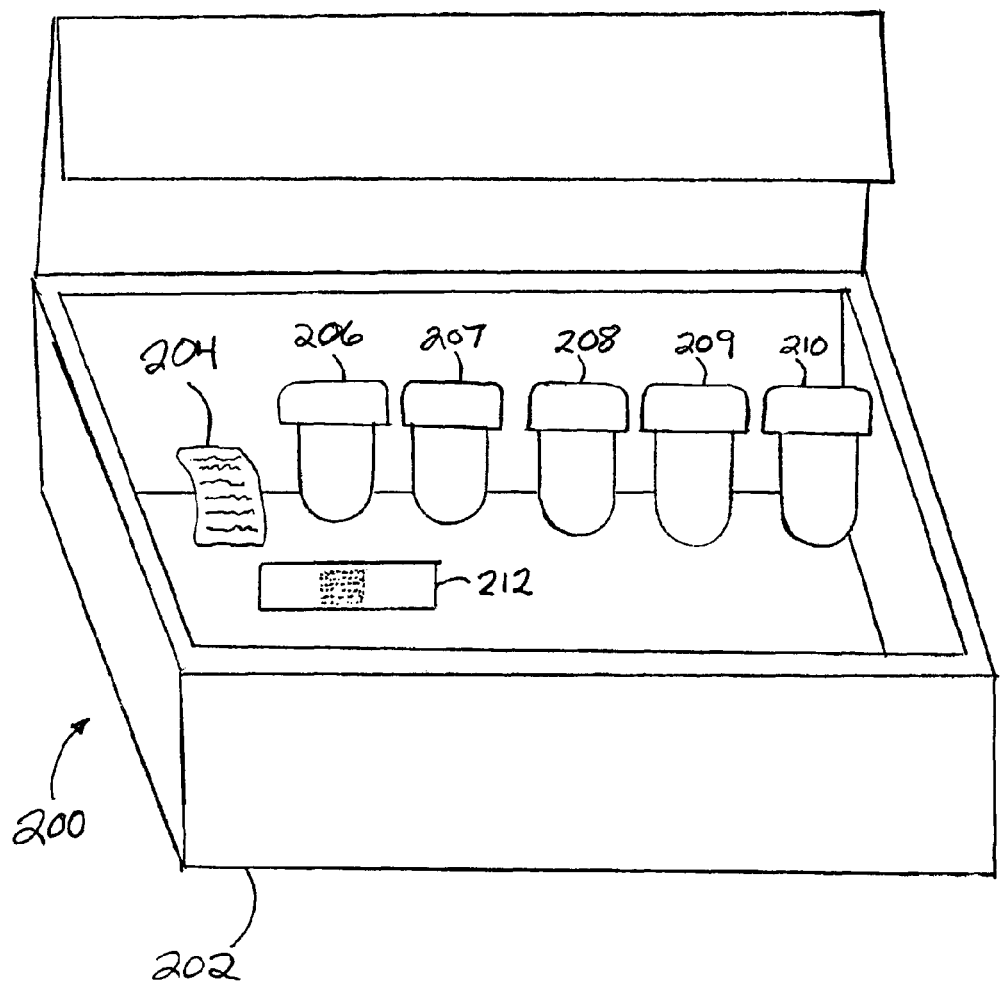
FIG. 5. Block diagram showing a representative example of a kit.

As described herein and shown in FIG. 5, in certain embodiments a kit 200 can include a housing 202 for housing various components. As shown in FIG. 5, and described herein, in one embodiment a kit 200 includes an aggregation sensor 206 as described herein and optionally one or more fluorescently labeled probe 207, one or more labels 208 that can be incorporated into an aggregant or other assay component, one or more intercalating dyes 209, one or more sensor biomolecules 210 and one or more substrates 212. As shown in FIG. 5, and described herein, the kit 200 can optionally include instructions 204. Other embodiments of the kit 200 wherein the components include various additional features described herein are within the scope of the invention.

EXAMPLES

The following examples are set forth so as to provide those of ordinary skill in the art with a complete description of how to make and use the present invention, and are not intended to limit the scope of what is regarded as the invention. Efforts have been made to ensure accuracy with respect to numbers used (e.g., amounts, temperature, etc.) but some experimental error and deviation should be accounted for. Unless otherwise indicated, parts are parts by weight, temperature is degree centigrade and pressure is at or near atmospheric, and all materials are commercially available.

Example 1

Synthesis of a Conjugated Polymeric Aggregation Sensor

The synthetic approach involved initially a Suzuki copolymerization of para-phenylenebisboronic acid with a 95:5 mixture of 2,7-dibromo-9,9-bis(6'-bromohexyl)fluorene and 4,7-dibromo-2,1,3-benzothiadiazole.[17] Elemental analysis of the resulting polymer is consistent with a chemical composition similar to the monomer feed. Since the GPC determined molecular weight ($M_n$) was ~11,000 amu, one can estimate that there is, on average, one BT molecule per polymer chain. In a second step, quaternization of the pendant groups by addition of $NMe_3$ provides the polycationic water soluble PFPB (see Scheme 1).

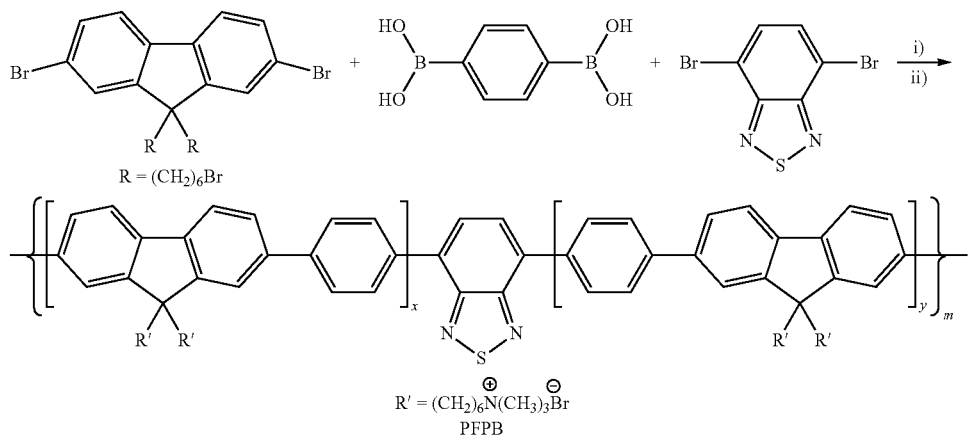

$^a$i) 2M $K_2CO_3$, THF, Pd(PPh$_3$)$_4$; ii) N(CH$_3$)$_3$, THF/H$_2$O.

General Details. 1H and 13C NMR spectra were collected on Varian ASM 200 MHz spectrometers. UV-Vis absorption spectra were recorded on a Shimadzu UV-2401 PC diode array spectrometer. Photoluminescence spectra were obtained using a Spex Fluorolog 2 spectrometer, using 90 degree angle detection for solution samples. Elemental analysis were performed by the UC Santa Barbara elemental analysis center. Reagents were obtained from Aldrich Co., and used as received.

4,7-dibromo-2,1,3-benzothiadiazole. 2,1,3-benzothiadiazole (6.8 g, 50 mmol) in 15 mL of 47% HBr solution was heated to reflux while bromine (24 g, 150 mmol) was added dropwise. At the end of the addition, an extra 10 mL of HBr was added, and the mixture was heated under reflux for an additional three hours. The mixture was filtered while hot, and the filtrate was washed with water, 5% sodium bicarbonate and water. The crude product was collected, dried, and recrystallized from chloroform-hexane to afford 4,7-dibromo-2,1,3-benzothiadiazole (9.0 g, 61.2%) as yellow crystals. 1H NMR (CDCl3, 200 MHz): d 7.72 ppm.

Poly[9,9-bis(6'-bromohexyl)fluorene-co-1,4-phenylene-co-4,7-(2,1,3-benzothiadiazole)] (PFPB precursor). 2,7-Dibromo-9,9-bis(6'-bromohexyl)fluorene (306.8 mg, 0.475 mmol), 4,7-dibromo-2,1,3-benzothiadiazole (7.3 mg, 0.025 mmol), 1,4-phenyldiboronic acid (82.9 mg, 0.5 mmol), Pd(PPh3)4 (8 mg) and potassium carbonate (830 mg, 6 mmol) were placed in a 25 mL round bottom flask. A mixture of water (3 mL) and THF (6 mL) was added to the flask and the reaction vessel was degassed. The mixture was refluxed at 85° C. for 20 h under nitrogen, and then precipitated into methanol. The polymer was filtered and washed with methanol and acetone, and then dried under vacuum for 24 h to afford the neutral PFPB precursor (180 mg, 65.9%), as a light yellow fibrous solid. 1H NMR (200 MHz, CDCl3): d 7.8 (m, 5H), 7.7-7.5 (m, 5H), 3.3 (t, 4H), 2.1 (m, 4H), 1.7 (br, 4H), 1.3-1.2 (m, 8H), 0.8 (br, 4H). Elemental analysis: Calcd for C, 15.025; H16.3Br0.95N0.05S0.025: C, 65.79; H, 5.98; N, 0.26. Found: C, 64.52; H, 5.39; N, 0.39. GPC (THF, polystyrene standard), Mw: 19,500 g/mol; Mn: 11,000 g/mol; PDI: 1.95.

Poly(9,9-bis(6'-N,N,N-trimethylammoniumbromide)hexyl)fluorene-co-1,4-phenylene-co-4,7-(2,1,3-benzothiadiazole)] (PFPB). Condensed trimethylamine (2 mL) was added dropwise to a solution of the neutral precursor polymer (50 mg) in THF (10 mL) at −78° C. The mixture was allowed to warm up to room temperature. The precipitate was re-dissolved by addition of water (10 mL). After the mixture was cooled down to −78° C., extra trimethylamine (2 mL) was added and the mixture was stirred for 24 h at room temperature. After removing most of the solvent, acetone was added to precipitate PFPB (55 mg, 91.2%) as a light yellow powder. 1H NMR (200 MHz, CD3OD): δ 8.1-7.7 (m, 10H), 3.3-3.2 (t, 4H), 3.1 (s, 18H), 2.3 (br, 4H), 1.6 (br, 4H), 1.3 (br, 8H), 0.8 (br, 4H).

Example 2

Demonstration of an Aggregation Sensor

In deionized water, at concentrations below $1\times10^{-6}$ M (in repeat units, RUs), PFPB emits predominantly in the 400 to 500 nm region, with a fluorescence quantum yield (Φ) of 22%. Indeed, both the absorption ($\lambda_{max}$=380 nm) and the emission are nearly identical to that of poly(9,9-bis(6'-N,N,N,-trimethylammoniumbromide)hexyl)fluorene-co-alt-1,4-phenylene) (PFP), which lacks BT sites (see FIGS. 1A and 1B).[18]

Under dilute conditions, the emission of PFPB is dominated by the more abundant oligo(fluorene-co-phenylene) segments. When [PFPB]>$1\times10^{-6}$ M, one observes the emergence of green emission (500 to 650 nm) characteristic of the BT sites. As [PFPB] increases, the green emission grows at the expense of the blue emission. These data indicate aggregation in the more concentrated regime, which leads to a reduction of the distance between polymer segments and enhances energy transfer to units containing lower energy BT chromophores.[19,20]

Example 3

General Procedure for FRET Experiments

The oligonucleotide used in the single stranded DNA study was 5'-TR-ATC TTG ACT ATG TGG GTG(SEQ ID NO:1).

The extent of hybridization was verified by variable temperature absorbance spectroscopy. Fluorescence intensities were determined from the integrated areas under emission spectra of both the donor and the acceptor (Texas Red). Measurements were carried out in water at a fixed ss-DNA-TR concentration ([ss-DNATR]=2.0 E-8 M), by varying the polymer with concentration varying from 0 M to 2.3 E-7 M. The excitation wavelength for PFB and PFPB was chosen at 380 nm, and the emission intensity was corrected to reflect the difference in optical density for polymers. The PNA used in the DNA/PNA-Cy5 study corresponds to the sequence 5'-Cy5-CAG TCC AGT GAT ACG-3'(SEQ ID NO:2). It was annealed at 2° C. below its melting temperature for 25 minutes in the presence of an equimolar amount of its complementary 15 base pair ss-DNAc (5'-CGT ATC ACT GGA CTG-3'(SEQ ID NO:3)) and in an identical fashion with a noncomplementary 15 base ss-DNAn (5'-ACT GAC GAT AGA CTG-3'(SEQ ID NO:4)). The absorbance of the hybridized strands was measured to determine concentration before using in FRET experiments. The extent of hybridization was checked by variable temperature absorbance spectroscopy.

Example 4

Detection of Aggregate Formation using FRET

FIG. 1A shows the emission from PFPB/ss-DNA solutions upon addition of ss-DNA ([RU]=$5\times10^{-7}$ M, ss-DNA=(5'-ATC TTG ACT ATG TGG GTG CT(SEQ ID NO:5)), [ss-DNA] varies from 0 M to $2.7\times10^{-8}$ M). The complexation of PFPB with ss-DNA (5'-ATC TTG ACT ATG TGG GTG CT(SEQ ID NO:5)) in water[21] led to contraction and aggregation of polymer chains, a concomitant reduction of inter-segment distances, and an increase in FRET to the BT sites. The isosbestic point at 492 nm highlights the transition from blue to green emission with increasing [ssDNA].

Example 5

FRET Using an Aggregation Sensor in a Multicolor Assay

Figure 1B:
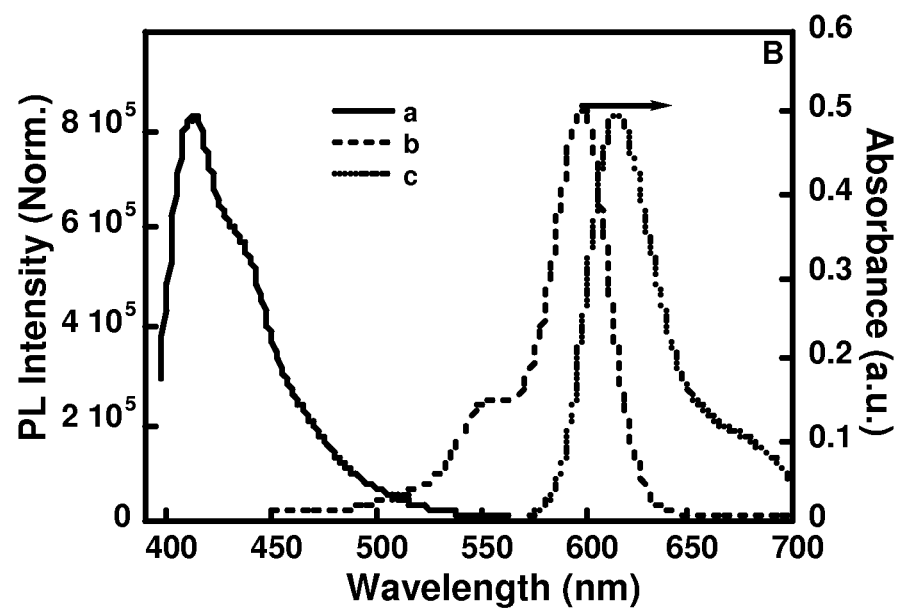
Figure 2:
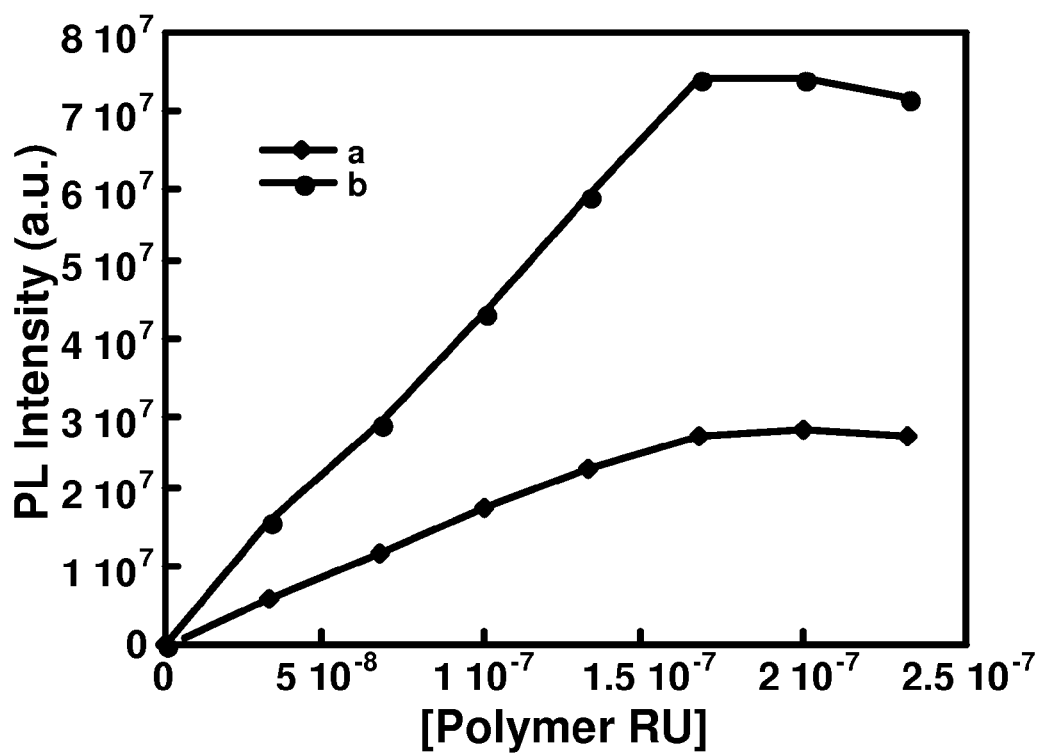
FIG. 2. TR emission intensity for PFP/ss-DNA-TR (a) and PFPB/ss-DNA-TR (b) in water ($\lambda_{exc}$=380 nm, [ss-DNA-TR]=2.0 E-8 M, TR intensity is corrected to reflect the difference in optical density for the two polymers).

FIG. 1B shows the emission spectra of PFP, and the absorption and emission of ss-DNA-TR (TR=Texas Red dye and ssDNA-TR=5'-TR-ATC TTG ACT ATG TGG GTG CT(SEQ ID NO:5)). Note that the spectral overlap between the absorption of TR and the green emission band of PFPB/ss-DNA is substantially larger than with the emission of PFP. Therefore, we anticipated a larger value for the overlap integral in the Förster equation and more efficient FRET with PFPB.[22] Indeed, as shown in FIG. 2, the TR emission intensity as a function of polymer concentration is much greater when PFPB is excited, relative to PFB (the value of Φ for TR is the same in the two sets of solutions). The spectra in FIG. 2 were measured by excitation at 380 nm, which selectively creates polymer-based excited states.

Based on the mechanistic information above, we postulated that PFPB could be used in a three color DNA assay by using a PNA-C* strand (where C* is a suitable fluorophore). PNA serves to provide a base sequence that searches for a complementary ssDNA. However, because PNA is neutral, it is possible to use water without buffers or other ions that are required to screen the negative charges during duplex formation.[23] Since PNA-TR is not commercially available, we used PNA-Cy5 (5'-Cy5-CAGTCCAGTGATACG(SEQ ID NO:2)) as the PNA-probe instead. The absorption and emission of Cy5 ($\lambda_{abs}$=648 nm, $\lambda_{en}$=681 nm) are similar to those of TR.

Hybridization of PNA-Cy5 with a complementary ss-DNA (ss-DNAc=5'-CGTATCACTGGACTG(SEQ ID NO:3)) endows the ss-DNAc/PNA-Cy5 duplex with multiple negative charges. Complexation of ss-DNAc/PNA-Cy5 by electrostatic forces to the positively charged PFPB allows for FRET from the polymer to Cy5 and should lead to red emission. In the case of a non-complementary ss-DNA (ss-DNAn=5'-ACTGACGATAGACTG(SEQ ID NO:4)), electrostatic complexation occurs only between PFPB and the ss-DNAn, which should give rise to emission from the BT units.

Figure 3:
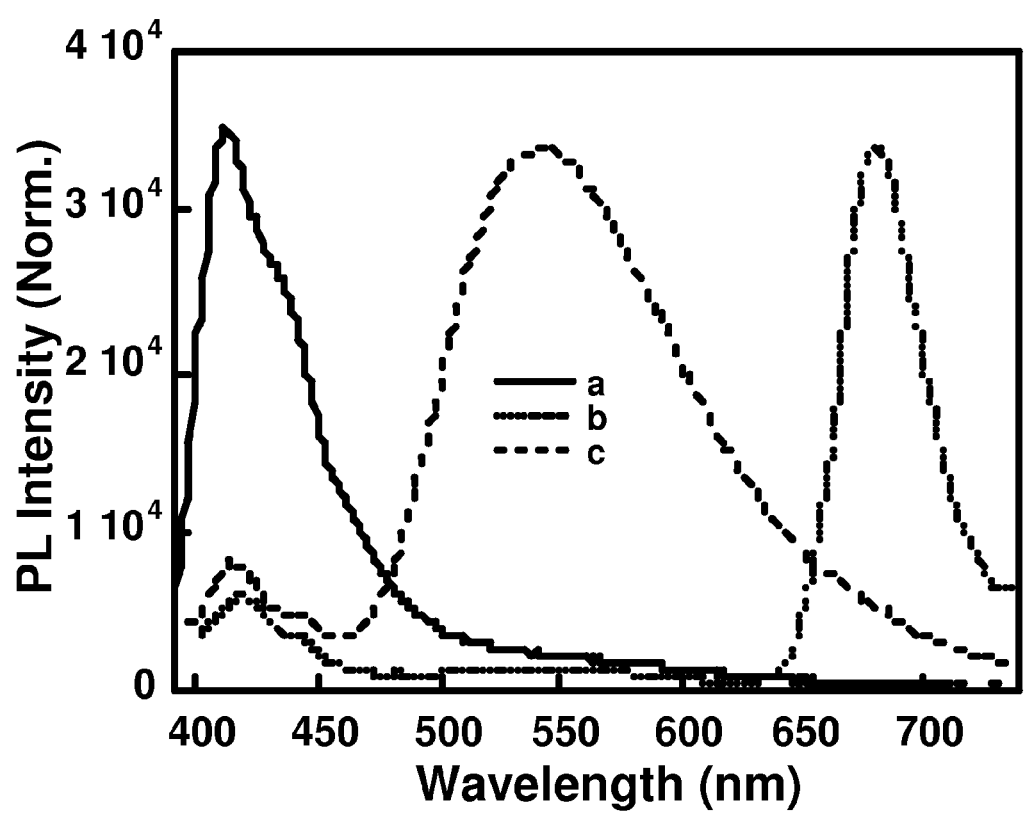
FIG. 3. Normalized fluorescence in water of PFPB/PNA-Cy5 (a), PFPB-DNAn/PNA-Cy5 (c) and PFPB-DNAc/PNA-Cy5 (b) ([PNA-Cy5]=2.0E-8 M, [RU]=1.6 E-7 M, ($\lambda_{exc}$=380 nm).

FIG. 3 shows the different emission colors observed in this detection scheme. In water (pH=7.0), a solution of PFPB ([RU]=1.6×10$^{-7}$ M) and PNA-Cy5 emits blue, indicating that no significant PFPB/PNA-Cy5 complexation takes place. For the non-complementary situation, i.e. ss-DNAn and PNA-Cy5 (annealing protocols are done independently), green emission is predominantly observed. Under similar conditions, when ss-DNAc/PNA-Cy5 is used, only red emission from the Cy5 units takes place. These data indicate that FRET from PFPB to the Cy5 signaling chromophore is essentially complete.

The above examples report design guidelines for water soluble conjugated polymer structures that change emission color depending on their state of aggregation. Complexation with oppositely charged polyelectrolytes (such as DNA) brings together polymer segments and encourages energy migration to low energy emissive sites (BT in the case of PFPB). Using a PNA-Cy5 probe strand, one obtains three different colors, depending on the solution content: blue, in the absence of DNA; green, when non-complementary ssDNA is present; and red, when the complementary ssDNA is found.

Example 6

Optimization of Polymer Structure and Quantitation of Polynucleotides

It occurred to us that the shift in emission color of PFPB materials could be used to determine the concentration of an aggregant such as dsDNA or ssDNA. In the absence of DNA, and under dilute conditions, the chains are isolated and emit blue. DNA-induced aggregation provides the molecular basis to modify FRET conditions and increase the green emission, at the expense of the blue color. By measuring the increase in green emission and/or the decrease in blue emission and applying calibration curves one can therefore calculate the total DNA concentration in the sample.

Initial efforts were directed towards optimization of polymer structure. PFPB structures with varying amounts of BT units were prepared as shown in Scheme 2. Suzuki cross-coupling mediated copolymerization of 2,7-dibromo-9,9-bis (6'-bromohexyl)fluorene, 1,4-phenylenebis(4,4,5,5-tetramethyl-1,3,2-dioxaborolane), and 4,7-dibromo-2,1,3-benzothiadiazole provides neutral precursor polymers in which the BT content is regulated by the ratio of 2,7-dibromo-9,9-bis(6'-bromohexyl)fluorene and 4,7-dibromo-2,1,3-benzothiadiazole. In a second step, quaternization with trimethylamine provides the water-soluble materials in greater than 90% yields after isolation. Using the procedure in Scheme 2, PFPB polymers were prepared with 1, 2.5, 5, and 7% BT contents. Efforts to obtain a material with 9% BT in this copolymer embodiment were unsuccessful, because low solubility in water prevented complete conversion at the quaternization step. The polymers were pale yellow in color and had virtually identical absorption spectra, with the maxima ranging from 378 nm to 383 nm. Each polymer had a small shoulder at 440 nm to 460 nm, attributable to the BT unit, which intensified with increased BT incorporation.

Scheme 2. i) K$_2$CO$_3$, THF/H$_2$O, Pd(dppf)Cl$_2$, reflux 48 h. ii) NMe$_3$, THF, MeOH, stir 48 h.

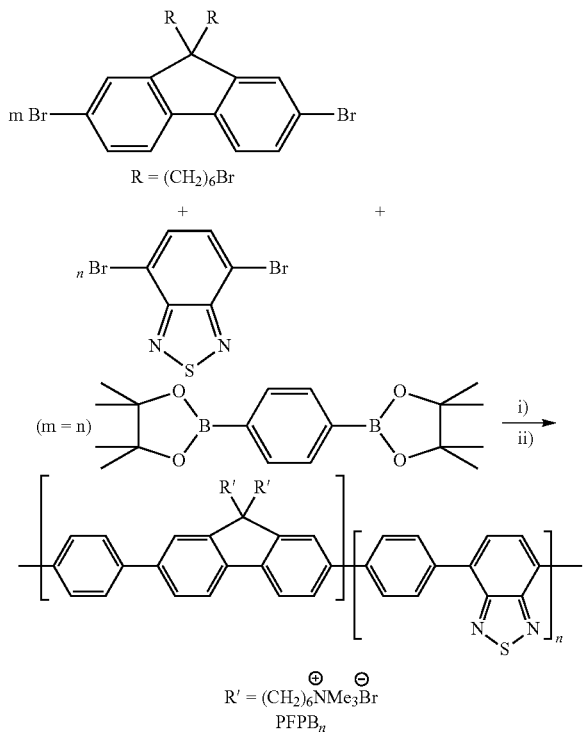

Figure 6:
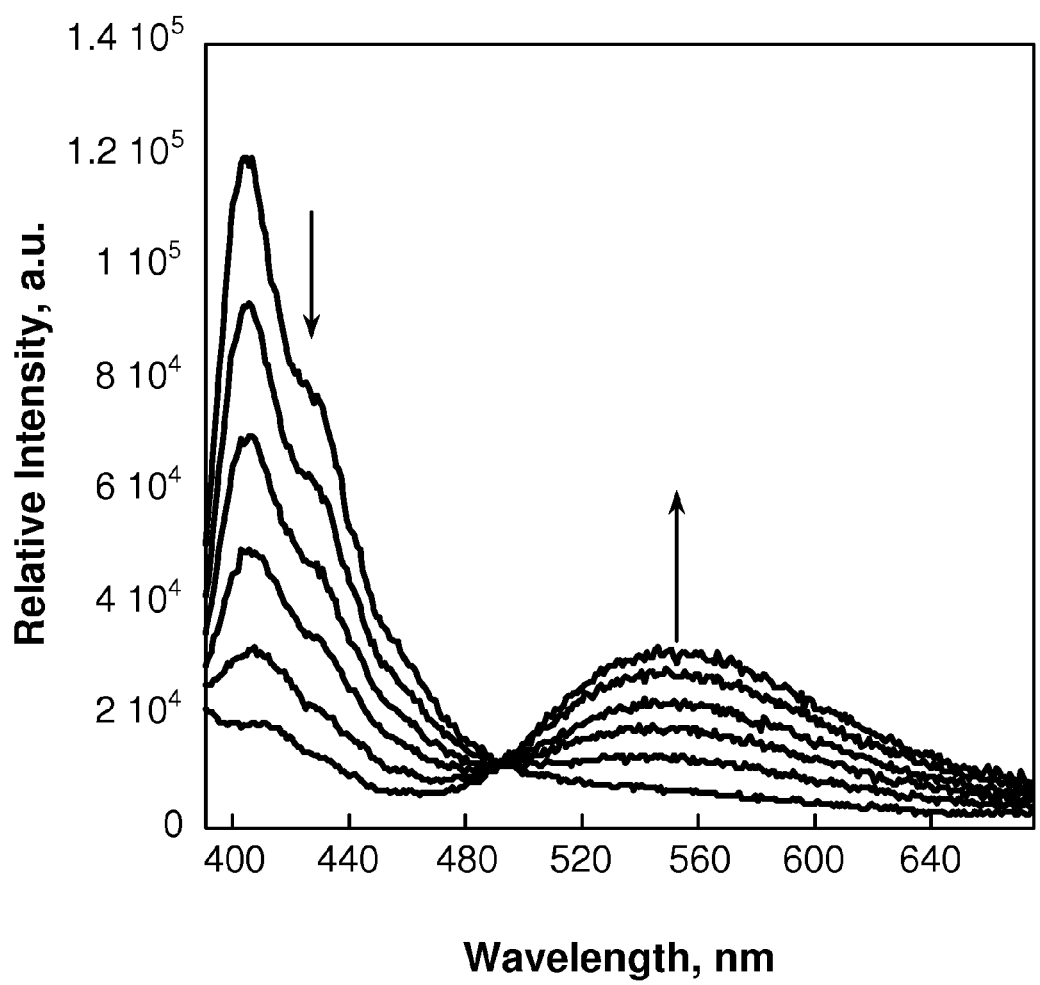
FIG. 6. PL spectra of PFPB$_7$ (1.0×10$^{-6}$ M) with 3.6 μL additions of 5.1×10$^{-6}$ M of 20 bp dsDNA ($\lambda_{ex}$=380 nm).

FIG. 6 shows the changes in the photoluminescence (PL) spectra of PFPB$_7$ (1.0×10$^{-6}$ M in fluorene-phenylene repeat units, RUs) in water upon addition of dsDNA in 6.2×10$^{-9}$ M increments up to a concentration of 9.6×10$^{-8}$ M (DNA concentration is made relative to base pairs for dsDNA and bases for ssDNA). As [dsDNA] increases, there is a progressive increase of the emission band at 550 nm and a concomitant decrease of the band at 410 nm. An isosbestic point is observed at 490 nm. This shift in emission color is attributed to the energy transfer from the main component of the conjugated backbone to the BT sites upon interpolyelectrolyte complex formation.

To obtain quantitative information on how the shift in emission color correlates to [DNA], we define the parameter δ, as shown in Equation 1, which incorporates information on spectral characteristics and provides a means to normalize data across different instruments and optical collection conditions:

$$\delta = \frac{G_n - G_0\left(\frac{B_n}{B_0}\right)}{N} \quad (1)$$

In Equation 1, $G_0$ is the integrated green fluorescence (500 nm to 700 nm) in the absence of DNA, and corresponds to the emission tail of PFPB$_x$ in this range, $G_n$ is the integrated green fluorescence at the nth addition of DNA, $B_0$ is the integrated blue fluorescence (390 nm to 480 nm) in the absence of DNA, $B_n$ is the integrated blue fluorescence at the nth addition of DNA and N is the normalization factor, obtained in our case by the emission (390 nm to 480 nm) of a $1.0\times10^{-6}$ M $PFPB_7$ which serves to compare measurements from instruments of different sensitivities and configurations.

Figure 7:
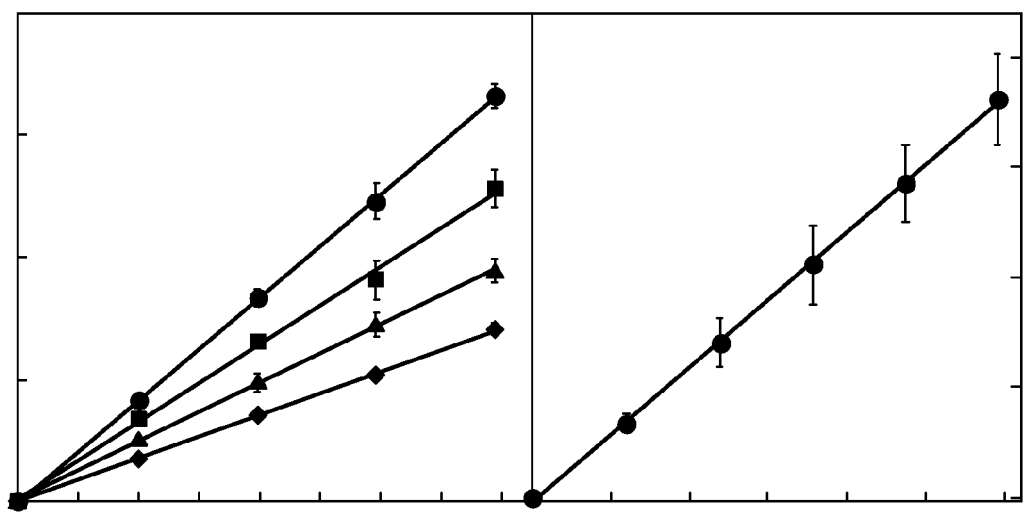
FIG. 7. (a) (left) δ for PFPB$_1$ (♦), PFPB$_{2.5}$ (▲), PFPB$_5$ (■) and PFPB$_7$ (●) as a function of by concentration for 30 bp dsDNA. (b) (right) δ for PFPB$_7$ (●) as a function of by concentration for 30 bp dsDNA in the concentration range of 6.0×10$^{-10}$ M to 3.0×10$^{-9}$ M.

A comparison of the responses of the different polymer compositions is given in FIG. 7(a) (left), where δ is plotted against [dsDNA]. Above all, for all structural compositions, there is a remarkable linear relationship between δ and [dsDNA] in this concentration range. Additionally, there is a direct correlation between the BT content in the backbone and the sensitivity of δ to [dsDNA]. As evidenced by the difference in slopes, $PFPB_1$ is the least responsive and $PFPB_7$ is the most responsive, with lower detection limits of $6.0\times10^{-10}$ M by (FIG. 7(b); right). That is to say, that at a given DNA concentration the shift from blue to green is more pronounced in the series $PFPB_7 > PFPB_5 > PFPB_{2.5} > PFPB_1$. Such a trend is expected on the basis of a greater concentration of green emitters and the greater propensity for aggregation based on the lower solubility of polymers with a larger fraction of BT units. Further experiments therefore used $PFPB_7$.

Figure 8:
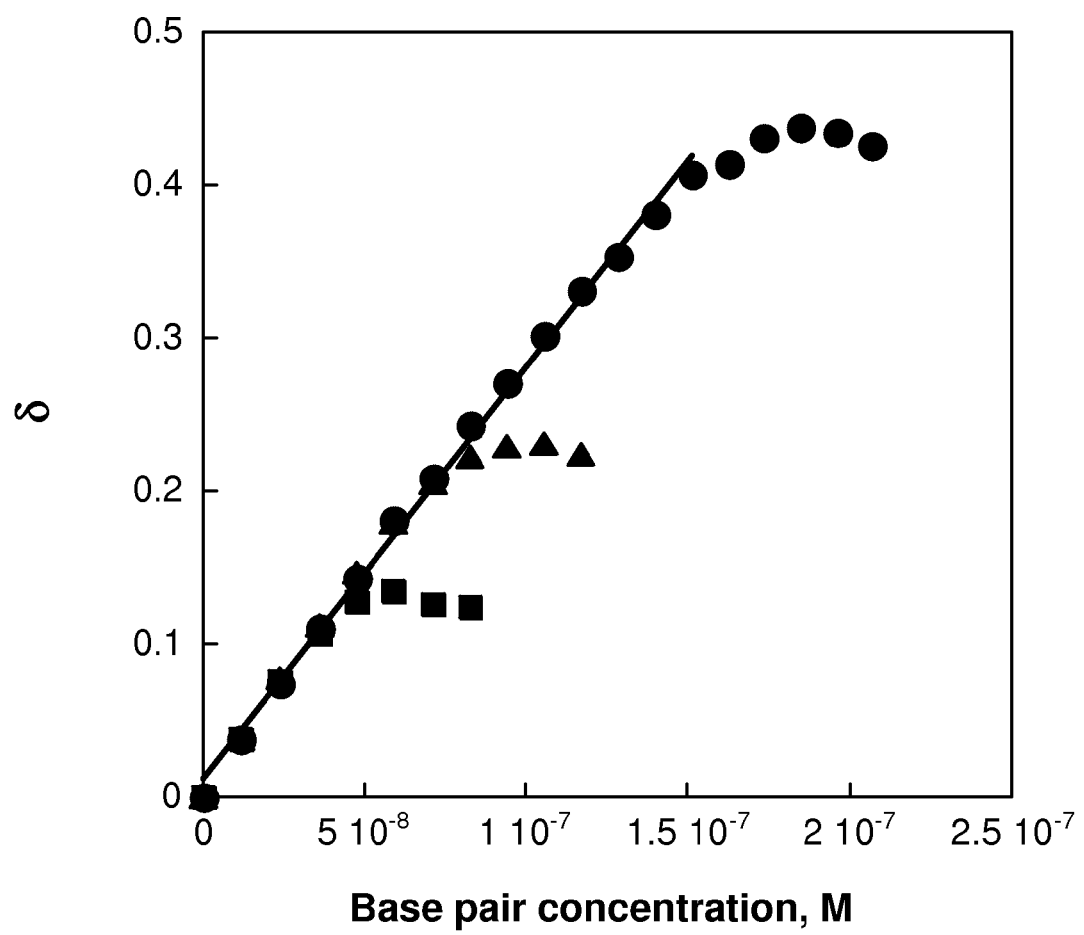
FIG. 8. δ as a function of by concentration of 30 bp dsDNA for PFPB$_7$ at [RU]=2.5×10$^{-7}$ M (■), 5.0×10$^{-7}$ M (▲), and 1.0×10$^{-6}$ M (●).

Two significant features are illustrated in FIG. 8, which shows the 8 response to 30 bp dsDNA at three different $PFPB_7$ concentrations (in RUs: of $2.5\times10^{-7}$ M, $5.0\times10^{-7}$ M, and $1.0\times10^{-6}$ M). First, the similar slopes in the low concentration regime ([dsDNA]<$5\times10^{-8}$ M) reveal that the response of the assay is independent of [$PFPB_7$]. Second, a leveling off of 8 vs. [dsDNA] takes place at higher [dsDNA]. This deviation from the initial linear relationship suggests a stoichiometric limit for the polyelectrolyte complex. Indeed, response saturation occurs when the RU/bp ratio is approximately 6, regardless of the total [RU]. Once this ratio is reached, there is no longer an increase in response from $PFPB_7$, and an upper limit for the response range is reached. We also note that it is not feasible to use more concentrated $PFPB_7$ solutions to extend the assay to more concentrated DNA regimes because $PFPB_7$ aggregation leads to BT emission in the absence of DNA.

Figure 9:
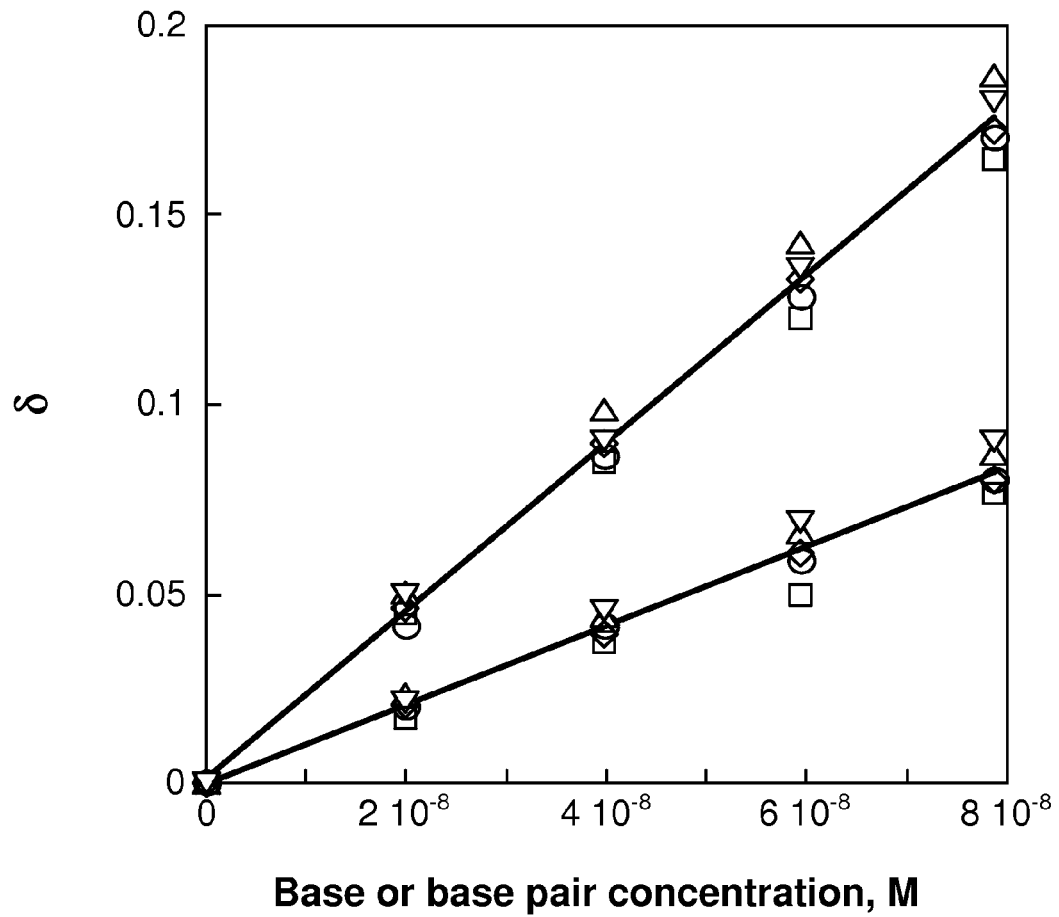
FIG. 9. δ as a function of [b] or [bp] for ssDNA (ss20-Δ; ss30-○; ss50-◇; ss75-▽; ss100-□) and dsDNA (ds20-Δ; ds30-○; ds50-◇; ds75-▽; ds100-□), respectively.

Possible changes brought about by differences in DNA chain length were examined by comparing ssDNA and dsDNA ranging from 20 to 100 bases or base pairs, respectively. FIG. 9 shows δ as a function of [ssDNA] or [dsDNA] using $PFPB_7$ at each of the different DNA lengths. Significantly, the specific length of the DNA is not a factor in modifying the δ response, as each of the data points falls on the same line, regardless of strand length. The responses of $PFPB_7$ for each DNA length are in close agreement with each other, with a standard deviation of ~8%. As expected, the slope for dsDNA is approximately twice that of the ssDNA due to the doubling of charge density.

Example 7

Comparison to Commercial Dyes

PicoGreen and OliGreen are widely used commercially available probes for the determination of [dsDNA] and [ssDNA]. Both reagents are based on cyanine dyes and are suspected to intercalate or otherwise bind irreversibly to DNA. This poses potential health and environmental hazards; consequently, containment is important and disposal involves the adsorption of the dyes on activated charcoal, followed by incineration. Picogreen has a lower detection limit of 25 pg/mL ($3.8\times10^{-11}$ M bp) of dsDNA and OliGreen has a lower detection limit of 100 pg/mL ($3.2\times10^{-10}$ M b) of ssDNA. In comparison, $PFPB_7$ has a lower detection limit of $6.0\times10^{-10}$ M by for dsDNA (FIG. 7(b), but exhibits viability due to its excellent accuracy and repeatability. Additionally, $PFPB_7$ shows greater efficiency in terms of photoluminescence yield. For a concentration of $2.0\times10^{-8}$ M 30 bp dsDNA, the relative photoluminescence yield (emission intensity/photons absorbed) of $PFPB_7$ is ~3 times more efficient than PicoGreen and similar to that of OliGreen. Another distinguishing feature of $PFPB_7$ is that it can be used to quantify both ssDNA and dsDNA.

While $PFPB_7$ shows several potential advantages over PicoGreen and OliGreen, the basis of this quantification assay on attractive electrostatic interactions makes it more susceptible both to charge screening and pre-aggregation in a buffered environment. Assays carried out with salt concentrations of up to 1 mM are unaffected. However, higher salt concentrations give rise to pre-aggregation, resulting in a shift of blue to green emission prior to DNA addition.

In summary, changes in the PL color of an aggregation sensor can be used to determine the concentration of ssDNA and dsDNA accurately, reliably and efficiently. Highest sensitivity was observed with $PFPB_7$, which contains the highest concentration of BT units in the backbone while keeping the polymer sufficiently soluble in water. Use of $PFPB_7$ aggregation induced by polyelectrolyte complexation eliminates the safety hazards associated with intercalating dyes. Because the intensity of the signaling event is based on the charge density of a target, future efforts can be directed towards development of similar quantification schemes for other negatively charged polyelectrolytes such as RNA, proteins or enzymes. Furthermore, we note that the range of this quantification approach can be broadened by the design of negatively charged PFPB analogs, such that biomolecules with multiple positive charges can also be included as targets.

Methods for Examples 6 and 7

General details. $^1$H and $^{13}$C NMR spectra were collected on a Varian Inova 400 MHz NMR. Fluorescence measurements were recorded on a PTI Quantamaster 4 spectrometer or a Jasco FP-6300 spectrometer at 90° detection angles. Absorption measurements to quantify [DNA] and [RU] were recorded on a Beckman Coulter DU 800 UV-Vis spectrometer and a Shimadzu UV-2401 UV-Vis spectrometer, respectively. DNA was purchased from GenScript or Integrated DNA Technologies and HPLC purified. Sequences used in this study were a statistical distribution of the four bases. PicoGreen and OliGreen kits were purchased from Molecular Probes. All FRET experiments were conducted in Milli-Pore water filtered with a Barnstead NANOpure II filtration system.

The percentages of BT groups incorporated in $PFPB_x$ were estimated by absorption spectra. Increased absorption of the BT group of the polymer could be seen as the BT to fluorene ratio in the polymer synthesis was varied. Quantum yield of fluorescence, $\Phi_{PL}$, was measured using fluorescein in water (pH 10) as the standard. Error associated with this measurement is ±0.05.

Synthetic details. Detailed procedures for the synthesis of $PFPB_5$ and precursors have been previously reported. Syntheses of $PFPB_1$, $PFPB_{2.5}$, $PFPB_5$, and $PFPB_7$ followed similar procedures, and composition was adjusted by varying the BT to fluorene feed ratio. The NMR data is shown for $PFPB_7$ and its precursor. $PFPB_7$ precursor. $^1$H NMR (400 MHz, CDCl$_3$): δ=7.9-7.6 (m, 10.5H), 3.316 (t, J=6.8 Hz, 4H), 2.112 (br s, 4H), 1.708 (m, 4H), 1.265 (br s, 4H), 1.161 (br s, 4H), 0.807 (br s, 4H). $^{13}$C NMR (100 MHz, CDCl$_3$): δ=151.624, 140.601, 140.373, 139.895, 127.817, 126.338, 121.543, 120.451, 55.419, 42.961, 34.267, 32.856, 29.321, 27.993, 23.904. $PFPB_7$. $^1$H NMR (400 MHz, CDCl$_3$): δ=8.0-7.6 (m, 10.5H), 3.081 (m, 4H), 2.902 (m, 18H), 2.131 (br s, 4H), 1.471 (br s, 4H), 1.103 (br s, 8H), 0.645 (br s, 4H). $\Phi_{PL}$=0.13.

General procedure for FRET experiments and analysis. Spectra were recorded in the following manner: 1.5 mL of a solution of known [RU] was prepared in a plastic cuvette. Before the introduction of DNA, the fluorescence was measured (390 nm to 700 nm), after which aliquots of a known concentration of DNA were added. Spectra were recorded after each subsequent addition. Analysis of data followed Equation 1.

Although the invention has been described in some detail with reference to the preferred embodiments, those of skill in the art will realize, in light of the teachings herein, that certain changes and modifications can be made without departing from the spirit and scope of the invention. Accordingly, the invention is limited only by the claims.

REFERENCES

[1] Gillespie, D. and Spiegelman, S., J. Mol. Biol. 1965 12, 829.
[2] Lipshutz, R. J.; Fodor, S. P. A.; Gingeras, T. R.; Lockart, D. J., Nature Genet. 1999, 21, 20.
[3] Wolcott, M. J. Clin. Microbiol. Rev. 1992, 5, 370.
[4] (a) Wang, J. Nucleic Acid Res. 2000, 28, 3011. (b) Umek, R. M.; Lin, S. W.; Vielmetter, J.; Terbrueggen, R. H.; Irvine, B.; Yu, C. J.; Kayyem, J. F.; Yowanto, H.; Blackburn, G. F.; Farkas, D. H.; Chen, Y. P. J. Mol. Diag. 2001, 3, 74. (c) Schork N. J.; Fallin D.; Lanchbury J. S. Clin. Genet. 2000, 58, 250.
[5] (a) Balakin, K. V.; Korshun, V. A.; Mikhalev, I. I.; Maleev, G. V.; Malakhov A. D.; Prokhorenko, I. A.; Berlin, Yu. A. Biosensors and Bioelectronics 1998, 13, 771.
[6] Ranade, K.; Chang, M. S.; Ting, C. T.; Pei, D.; Hsiao, C. F.; Olivier, M.; Pesich, R.; Hebert, J.; Chen, Y. D.; Dzau, V. J.; Curb, D.; Olshen, R.; Risch, N.; Cox, D. R.; Botstein, D., Genome Res. 2001, 11, 1262.
[7] Piatek, A. S.; Tyagi, S.; Pol, A. C.; Telenti, A.; Miller, L. P.; Kramer, F. R.; Alland, D., Nat Biotechnol 1998, 16, 359.
[8] Wang, J. Nucleic Acid Res. 2000, 28, 3011.
[9] Umek, R. M.; Lin, S. W.; Vielmetter, J.; Terbrueggen, R. H.; Irvine, B.; Yu, C. J.; Kayyem, J. F.; Yowanto, H.; Blackburn, G. F.; Farkas, D. H.; Chen, Y. P. J. Mol. Diag. 2001, 3, 74.
[10] Schork N. J.; Fallin D.; Lanchbury J. S. Clini. Genet. 2000, 58, 250.
[11] Chen, L.; McBranch, D. W.; Wang, H. L.; Helgeson, R.; Wudl, F.; Whitten, D. G. Proc. Natl. Acad. Sci. U.S.A. 2000, 96, 12287.
[12] McQuade, D. T.; Pullen. A. E.; Swager, T. M. Chem. Rev. 2000, 100, 2537.
[13] Gaylord, B. S.; Heeger A. J.; Bazan G. C. Proc. Natl. Acad. Sci, U.S.A., 2002, 99, 10954.
[14] Gaylord, B. S.; Heeger A. J.; Bazan G. C. J. Am. Chem. Soc., 2003, 125, 896.
[15] Beljonne, D.; Pourtois, G.; Silva, C.; Hennebicq, E.; Herz, L. M.; Friend, R. H.; Scholes, G. D.; Setayesh, S.; Mullen, K.; Bredas, J. L. Proc. Natl. Acda. Sci, U.S.A., 2002, 99, 10982.
[16] Nguyen T. Q.; Wu, J. J.; Doan, V.; Schwartz, B. J.; Tolbert, S. H. Science, 2000, 288, 652.
[17] Liu, B.; Gaylord, B. S.; Wang, S.; Bazan G. C. J. Am. Chem. Soc., 2003, 125, 6705.
[18] Stork, M. S.; Gaylord, B. S.; Heeger, A. J.; Bazan, G. C. Adv. Mater. 2002, 14, 361.
[19] Miao, Y.-J.; Herkstroeter, W. G.; Sun, B. J.; Wong-Foy, A. G.; Bazan, G. C. J. Am. Chem. Soc. 1995, 117, 11407.
[20] Huang, J.; Niu, Y. H.; Yang, W.; Mo, Y. J.; Yuan, M.; Cao, Y. Macromolecules, 2002, 35, 6080.
[21] When 50 mmol phosphate buffer is used to make a solution of PFPB ($1\times10^{-6}$ M), green emission dominates, probably because of ion induced polymer aggregation.
[22] Lakowicz, J. R.; $2^{nd}$ ed., Principles of Fluorescence Spectroscopy. Kluwer Academic/Plenum Publisher. New York, 1999.
[23] Nielsen, P. E.; Egholm, M. Peptide Nucleic Acids: Protocols and Applications. Horizon Scientific Press, Portland, 1999.

What is claimed is:

1. A method of assaying a sample for an aggregant, the method comprising:
   providing an aggregation sensor soluble in a polar medium, the aggregation sensor comprising
   (a) a polymer comprising
      a plurality of first optically active units forming a conjugated system, having a first absorption wavelength at which the first optically active units absorb light to form an excited state that can emit light of a first emission wavelength, and
      a plurality of solubilizing functionalities; and
   (b) one or more second optically active units that can receive energy from the excited state of the first optically active unit;
      said aggregation sensor comprising at least three first optically active units per second optically active unit, wherein a solution of the aggregation sensor emits detectably less light at the first emission wavelength when the concentration of first optically active units within energy-transferring distance of at least one second optically active unit is increased;
   combining the aggregation sensor and the sample in solution, wherein the aggregation sensor is present at a concentration at which there is detectable emission at the first emission wavelength in the absence of sample;
   contacting the aggregation sensor with light of the first absorption wavelength; and
   detecting whether the optical properties of the aggregation sensor are altered in the presence of the sample,
   wherein the second optically active unit is grafted to the conjugated system and forms part of the conjugated system.

2. The method of claim 1, where detecting whether the optical properties of the aggregation sensor are altered in the presence of the sample comprises detecting if the aggregation sensor emits less light of the first emission wavelength.

3. The method of claim 1, where the second optically active unit forms an excited state upon receiving energy from the first optically active unit and emits light of a second emission wavelength, and where detecting whether the optical properties of the aggregation sensor are altered in the presence of the sample comprises detecting if the solution emits light of the second emission wavelength.

4. The method of claim 3, further comprising combining a probe with the aggregation sensor and the sample in solution, wherein the probe binds specifically to a particular species of a class of aggregants that binds to the aggregation sensor, said probe attached to a fluorophore that receives energy from the second optically active unit when in proximity thereto and then emits light of a third emission wavelength, where detecting whether the optical properties of the aggregation sensor are altered in the presence of the sample comprises detecting if the solution emits light of the third emission wavelength.

5. The method of claim 4, wherein the amount of light emitted from the fluorophore is greater than can be achieved by direct excitation of the fluorophore with light of an appropriate wavelength.

6. The method of claim 4, wherein the probe comprises a component selected from the group consisting of a polypeptide, a polynucleotide, and a peptide nucleic acid (PNA).

7. The method of claim 1, further comprising combining an intercalating dye with the aggregation sensor and the sample in solution under conditions in which the dye intercalates with a sequence-specific duplex aggregate comprising a probe comprising a polynucleotide bound to a polynucleotide aggregant, wherein the intercalated dye exchanges energy with at least one other optically active species present in the aggregate when formed.

8. The method of claim 1, wherein the conjugated polymer comprises at least one optionally substituted repeat unit selected from the group consisting of 2,1,3-benzothiadiazole, benzoselenadiazole, naphthoselenadiazole, 4,7-di(thien-2-yl)-2,1,3-benzothiadiazole, an olefin, a cyano-substituted olefin, 2,7-carbazolene-vinylene, 2,7-fluorene, and 4,4'-biphenyl.

9. The method of claim 1, wherein the aggregation sensor comprises a conjugated polymer comprising optionally substituted poly(fluorene-co-phenylene) repeat units with 2,1,3-benzothiadiazole as the second optically active unit.

10. The method of claim 1, wherein the aggregation sensor comprises a ratio of first optically active units per second optically active units selected from the group consisting of at least four first optically active units per second optically active unit, at least six first optically active units per second optically active unit, at least nine first optically active units per second optically active unit, and at least nineteen first optically active units per second optically active unit.

11. The method of claim 1, wherein the aggregation sensor contains one second optically active unit.

12. The method of claim 1, wherein the first absorption wavelength is about 488 nm.

13. The method of claim 1, wherein the class of aggregants is selected from the group consisting of polypeptides and polynucleotides.

14. The method of claim 13, wherein the aggregant detected is a polynucleotide produced via an amplification reaction.

15. The method of claim 1, wherein a single nucleotide polymorphism (SNP) is detected in the aggregant.

16. The method of claim 1, wherein expression of a gene is detected upon detection of the aggregant.

17. The method of claim 1, wherein a result is used to diagnose a disease state of a patient.

18. The method of claim 17, wherein the use of the result to diagnose a disease state comprises reviewing or analyzing data relating to the presence of an aggregant in a sample; and providing a conclusion to a patient, a health care provider or a health care manager, the conclusion being based on the review or analysis of data regarding a disease diagnosis.

* * * * *

SEQUENCE LISTING

```
<160> NUMBER OF SEQ ID NOS: 5

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atcttgacta tgtgggtg                                                   18

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cagtccagtg atacg                                                      15

<210> SEQ ID NO 3
```

-continued

```
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cgtatcactg gactg                                                      15

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
actgacgata gactg                                                      15

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atcttgacta tgtgggtgct                                                 20
```